(12) United States Patent
Olsen

(10) Patent No.: US 7,758,568 B2
(45) Date of Patent: Jul. 20, 2010

(54) IMPLANTABLE THERAPEUTIC SUBSTANCE DELIVERY DEVICE

(75) Inventor: James M Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1389 days.

(21) Appl. No.: 10/854,974

(22) Filed: May 27, 2004

(65) Prior Publication Data

US 2004/0220553 A1    Nov. 4, 2004

Related U.S. Application Data

(63) Continuation of application No. 09/952,894, filed on Sep. 14, 2001, now Pat. No. 7,288,085.

(60) Provisional application No. 60/282,775, filed on Apr. 10, 2001.

(51) Int. Cl.
    *A61M 37/00*    (2006.01)
    *A61K 9/22*    (2006.01)
(52) U.S. Cl. .................. 604/891.1; 604/288.04
(58) Field of Classification Search ... 604/890.1–892.1, 604/65–67, 288.1–288.4, 131, 151, 152, 604/153, 154, 141
    See application file for complete search history.

(56) References Cited

U.S. PATENT DOCUMENTS

| | | | |
|---|---|---|---|
| 3,522,811 A | | 8/1970 | Schwartz et al. |
| 3,692,027 A | * | 9/1972 | Ellinwood, Jr. .......... 604/891.1 |
| 3,724,467 A | | 4/1973 | Avery et al. |

(Continued)

FOREIGN PATENT DOCUMENTS

CH        657275 A5    8/1986

(Continued)

OTHER PUBLICATIONS

"Valves, Piping & Pipelines Handbook," Elsevier Advanced Technology XP002200965, ISBN: 1 85617 252 X, Chapter Entitled Cavitation, pp. 658-666.

(Continued)

*Primary Examiner*—Matthew F DeSanto
(74) *Attorney, Agent, or Firm*—Mueting, Raasch & Gebhardt, P.A.

(57) ABSTRACT

A medical device known as an implantable therapeutic substance delivery device is configured for implanting in humans to deliver a therapeutic substance such as pharmaceutical compositions, genetic materials, and biologics to treat a variety of medical conditions such as pain, spastisity, cancer, and many other conditions. The therapeutic substance delivery device has a permanent magnet solenoid pump that is energy efficient, accurate, small, compatible with therapeutic substances, and has many other improvements. The implantable therapeutic substance delivery device has a housing, a therapeutic substance reservoir, a power source, electronics, and a permanent magnet solenoid pump. The therapeutic substance reservoir is configured to contain a therapeutic substance and is coupled to the housing. The power source is carried in the housing to power the electronics and solenoid pump. The electronics are coupled to the solenoid pump and the solenoid pump is coupled to the therapeutic substance reservoir. The permanent magnet solenoid pump is configured for pumping therapeutic substance from the therapeutic substance reservoir through an infusion outlet at a programmed infusion rate. Many embodiments of the permanent magnet solenoid pump and its methods of operation are possible.

20 Claims, 19 Drawing Sheets

U.S. PATENT DOCUMENTS

| | | | |
|---|---|---|---|
| 3,846,682 A | 11/1974 | Massie | |
| 4,071,042 A | 1/1978 | Lombard et al. | |
| 4,102,610 A | 7/1978 | Taboada et al. | |
| 4,210,409 A | 7/1980 | Child | |
| 4,437,815 A | 3/1984 | McMullen | |
| 4,487,603 A | 12/1984 | Harris | |
| 4,541,787 A | 9/1985 | DeLong | |
| 4,557,726 A | 12/1985 | Reinicke | |
| 4,568,250 A | 2/1986 | Falk et al. | |
| 4,569,641 A | 2/1986 | Falk et al. | |
| 4,636,150 A | 1/1987 | Falk et al. | |
| 4,690,371 A | 9/1987 | Bosley et al. | |
| 4,699,615 A * | 10/1987 | Fischell et al. | 604/131 |
| 4,714,462 A | 12/1987 | DiDomenico | |
| 4,775,301 A | 10/1988 | Cartwright et al. | |
| 4,883,467 A | 11/1989 | Franetzki et al. | |
| 4,965,864 A | 10/1990 | Roth et al. | |
| 4,985,015 A | 1/1991 | Obermann et al. | |
| 5,085,563 A | 2/1992 | Collins et al. | |
| 5,220,929 A | 6/1993 | Marquit | |
| 5,318,521 A | 6/1994 | Slettenmark | |
| 5,405,367 A | 4/1995 | Schulman et al. | |
| 5,434,549 A | 7/1995 | Hirabayashi et al. | |
| 5,462,525 A | 10/1995 | Srisathapat et al. | |
| 5,472,323 A | 12/1995 | Hirabayashi et al. | |
| 5,509,792 A | 4/1996 | Sullivan et al. | |
| 5,707,361 A | 1/1998 | Slettenmark | |
| 5,758,666 A | 6/1998 | Larson, Jr. et al. | |
| 5,782,798 A * | 7/1998 | Rise | 604/500 |
| 5,792,067 A | 8/1998 | Karell | |
| 5,797,733 A | 8/1998 | Falk et al. | |
| 5,814,095 A | 9/1998 | Müller et al. | |
| 5,833,440 A | 11/1998 | Berling | |
| RE36,120 E | 3/1999 | Karell | |
| 5,915,929 A | 6/1999 | Falk et al. | |
| 5,921,526 A | 7/1999 | Najmolhoda | |
| 5,938,689 A | 8/1999 | Fischell et al. | |
| 5,947,155 A | 9/1999 | Miki et al. | |
| 5,984,859 A | 11/1999 | Lesinski | |
| 6,006,124 A | 12/1999 | Fischell et al. | |
| 6,016,449 A | 1/2000 | Fischell et al. | |
| 6,061,593 A | 5/2000 | Fischell et al. | |
| 6,128,538 A | 10/2000 | Fischell et al. | |
| 6,134,474 A | 10/2000 | Fischell et al. | |
| 6,176,879 B1 | 1/2001 | Reischl et al. | |
| 6,230,049 B1 | 5/2001 | Fischell et al. | |
| 6,248,080 B1 | 6/2001 | Miesel et al. | |
| 6,259,951 B1 | 7/2001 | Kuzma et al. | |
| 6,321,126 B1 | 11/2001 | Kuzma | |
| 6,324,433 B1 | 11/2001 | Errico | |
| 6,353,754 B1 | 3/2002 | Fischell et al. | |
| 6,354,299 B1 | 3/2002 | Fischell et al. | |
| 6,358,281 B1 | 3/2002 | Berrang et al. | |
| 6,360,122 B1 | 3/2002 | Fischell et al. | |
| 6,366,813 B1 | 4/2002 | DiLorenzo | |
| 6,409,698 B1 * | 6/2002 | Robinson et al. | 604/19 |
| 6,415,184 B1 | 7/2002 | Ishikawa et al. | |
| 6,456,886 B1 | 9/2002 | Howard, III et al. | |
| 6,480,743 B1 | 11/2002 | Kirkpatrick et al. | |
| 6,516,808 B2 | 2/2003 | Schulman | |
| 6,560,486 B1 | 5/2003 | Osorio et al. | |
| 6,569,195 B2 | 5/2003 | Yang et al. | |
| 6,647,296 B2 | 11/2003 | Fischell et al. | |
| 6,648,914 B2 | 11/2003 | Berrang et al. | |
| 6,726,678 B1 | 4/2004 | Nelson et al. | |
| 6,782,292 B2 | 8/2004 | Whitehurst | |
| 2001/0051819 A1 | 12/2001 | Fischell et al. | |
| 2002/0002390 A1 | 1/2002 | Fischell et al. | |
| 2002/0013612 A1 | 1/2002 | Whitehurst | |
| 2002/0019669 A1 | 2/2002 | Berrang et al. | |
| 2002/0072770 A1 | 6/2002 | Pless | |
| 2002/0077670 A1 | 6/2002 | Archer et al. | |
| 2002/0099412 A1 | 7/2002 | Fischell et al. | |
| 2002/0161403 A1 | 10/2002 | Meadows et al. | |
| 2002/0169485 A1 | 11/2002 | Pless et al. | |
| 2002/0173773 A1 | 11/2002 | Olsen | |
| 2002/0177882 A1 | 11/2002 | DiLorenzo | |
| 2003/0004428 A1 | 1/2003 | Pless et al. | |
| 2003/0109903 A1 | 6/2003 | Berrang et al. | |
| 2004/0172090 A1 | 9/2004 | Janzig et al. | |
| 2004/0173221 A1 | 9/2004 | Singhal et al. | |
| 2004/0176673 A1 | 9/2004 | Wahlstrand et al. | |
| 2004/0176814 A1 | 9/2004 | Singhal et al. | |
| 2004/0176815 A1 | 9/2004 | Janzig et al. | |
| 2004/0176816 A1 | 9/2004 | Singhal et al. | |
| 2004/0176818 A1 | 9/2004 | Wahlstrand et al. | |
| 2004/0176819 A1 | 9/2004 | Wahlstrand et al. | |
| 2004/0220518 A1 | 11/2004 | Heruth et al. | |

FOREIGN PATENT DOCUMENTS

| | | |
|---|---|---|
| EP | 0605903 B1 | 7/1994 |
| EP | 0791369 A1 | 8/1997 |
| EP | 1145735 A2 | 10/2001 |
| EP | 1145736 A2 | 10/2001 |
| EP | 1145735 A3 | 4/2004 |
| EP | 1145736 A3 | 4/2004 |
| JP | 55-142981 | 11/1980 |
| JP | 55142981 | 11/1980 |
| WO | WO 00/40295 A1 | 7/2000 |
| WO | WO 01/28622 A2 | 4/2001 |
| WO | WO 01/39830 A2 | 6/2001 |
| WO | WO 01/39830 A3 | 6/2001 |
| WO | WO 01/60450 A1 | 8/2001 |
| WO | WO 02/083207 A1 | 10/2002 |
| WO | WO 02/083208 A2 | 10/2002 |
| WO | WO 02/083208 A3 | 10/2002 |
| WO | WO 02/083233 A2 | 10/2002 |

OTHER PUBLICATIONS

"SynchroMed® Infusion System," product brochure, 1995, 4 pgs.

* cited by examiner

Two Coils and One Magnet

Three Coils and Two Magnets

IMPLANTABLE THERAPEUTIC SUBSTANCE DELIVERY DEVICE

RELATED APPLICATIONS

This application is a continuation of U.S. patent application Ser. No. 09/952,894, filed Sep. 14, 2001, now U.S. Pat. No. 7,288,085, issued Oct. 30, 2007, which claims the benefit of provisional application U.S. Ser. No. 60/282,775, filed Apr. 10, 2001, entitled "PERMANENT MAGNET SOLENOID PUMP FOR AN IMPLANTABLE THERAPEUTIC SUBSTANCE DELIVERY DEVICE," by James M. Olsen. Both of these applications are hereby incorporated by reference in their respective entireties.

BACKGROUND OF THE INVENTION

This disclosure relates to a medical device and more particularly to an implantable therapeutic substance delivery device with a piston operated pump.

The medical device industry produces a wide variety of electronic and mechanical devices for treating patient medical conditions such as pacemakers, defribulators, neurostimulators, and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. Implantable drug delivery pumps can be used to treat conditions such as pain, spasticity, cancer, and a wide variety of other medical conditions.

An implantable drug delivery pump is implanted by a clinician into a patient at a location appropriate for the therapy that interferes as little as practicable with patient activity such as subcutaneous in the lower abdomen. Typically, a drug delivery catheter is connected to the drug pump outlet and implanted to infuse the drug, infusate or other therapeutic substance at a programmed infusion rate and predetermined location to treat the medical condition. Reliable and accurate operation of the drug pump is important because both inadequate and unintended therapeutic substance delivery can create patient complications. Many drug pumps are configured, so the pump can be replenished with drug through a refill port or septum while the pump is implanted, so the period the pump can be implanted may not be limited by drug capacity. In electrically powered implantable drug pumps, the period the pump can be implanted is often limited by factors such as battery consumption, corrosive damage, and mechanical wear. The relative large size of some implantable drug pumps can limit locations where the device can be implanted in a patient. An example of an implantable drug pump is shown in Medtronic, Inc. "SynchroMed® Infion System" Product Brochure (1995). Implantable drug pumps can use a variety of pumping mechanism such as a piston pump, rotary vane pump, osmotic pump, Micro Electro Mechanical Systems (MEMS) pump, diaphragm pump, peristaltic pump, and solenoid piston pump to infuse a drug into a patient.

Peristaltic pumps typically operate by a battery powered electric motor that drives peristaltic rollers over a flexible tube having one end coupled to a therapeutic substance reservoir and the other end coupled to an infusion outlet to pump the therapeutic substance from the therapeutic substance reservoir through the infusion outlet. An implantable peristaltic pump typically consumes energy at about 6 Joules per milliliter (J/ml) of fluid pumped. Peristaltic pumps are typically about 3% efficient in terms of electrical energy input and fluid work output. In an implantable therapeutic substance delivery device having a peristaltic pump, the peristaltic pump is typically one of the largest components in the device and can consume 90% or more of the available battery power. The flexible tube used in a peristaltic pump is typically permeable to some therapeutic substance components such as water that can then infiltrate into the hermetically sealed housing and cause corrosion. Additionally, the flexible tube can expand resulting in decreased accuracy.

Solenoid piston pumps such as variable reluctance solenoid pumps and permanent magnet solenoid pumps can have disadvantages compared to peristaltic pumps such as higher energy consumption, difficulty with passing air, difficulty with valve sealing, and therapeutic substance material compatibility. Energy consumption of a reluctance solenoid pump can be relatively high because of pump construction and nonlinear piston force. Reluctance solenoid pumps can be constructed with a large pole piece that can cause fluid energy loss. Reluctance solenoid pump nonlinear piston force caused when piston force increases as the poles close the gap can also reduce pumping efficiency. Passing air can be difficult for solenoid pumps because of large dead volumes created by valve geometries. Sealing valves can be difficult because passively operated valves can unintentionally open under some circumstances creating safety concerns. Therapeutic substance material compatibility can be difficult to achieve in some solenoid pumps because of the pumping components that are in contact with the therapeutic substance. Examples of previous solenoid pumps are shown in U.S. Pat. No. 4,883,467 "Reciprocating Pump For An Implantable Medication Dosage Device" by Franetzki et al. (Nov. 28, 1989) and U.S. Pat. No. 4,569,641 "Low Power Electromagnetic Pump" by Falk et al. (Feb. 11, 1986). An example of a permanent magnet pump configured for pumping liquids such as water or kerosene is shown in U.S. Pat. No. 5,472,323 "Moveable Magnet Type Pump" by Hirabayashi et al. (Dec. 5, 1995).

For the foregoing reasons, there is a need for a permanent magnet pump for an implantable therapeutic substance delivery device that is energy efficient, small, compatible with therapeutic substances, and has many other improvements.

SUMMARY OF THE INVENTION

A permanent magnet solenoid pump for an implantable therapeutic substance delivery device embodiment is energy efficient, accurate, small, compatible with therapeutic substances, and has many other improvements. The permanent magnet solenoid pump is coupled to electronics and coupled to a therapeutic substance reservoir outlet to pump therapeutic substance from the therapeutic substance reservoir through an infusion outlet at a programmed rate. The permanent magnet solenoid pump is carried in a therapeutic substance delivery device that has a housing, a therapeutic substance reservoir coupled to the housing, a power source carried in the housing, and electronics carried in the housing and coupled to the power source. Many embodiments of the permanent magnet solenoid pump and its methods of operation are possible.

DETAILED DESCRIPTION OF THE PREFERRED EMBODIMENTS

Figure 1:
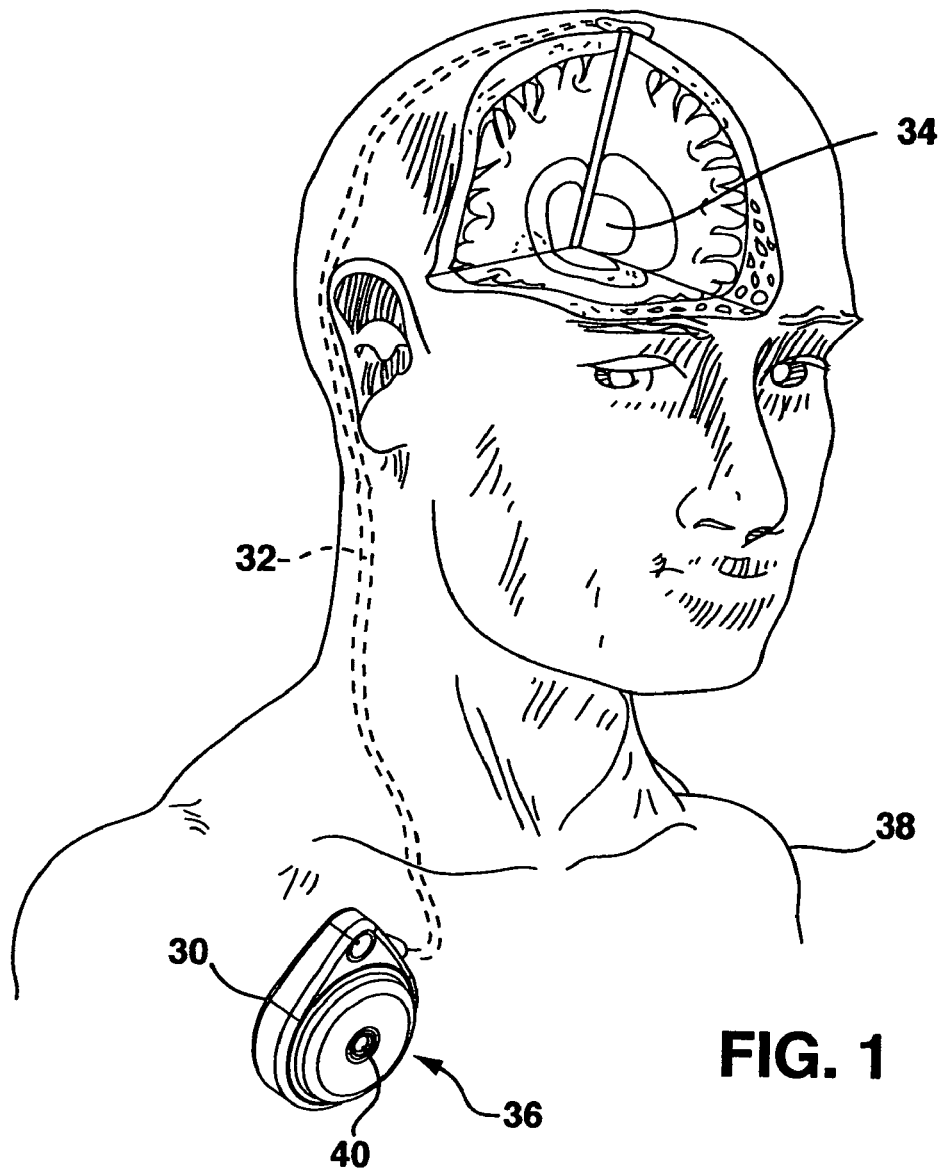
FIG. 1 shows the environment of an implantable therapeutic substance delivery device embodiment.
Figure 2:
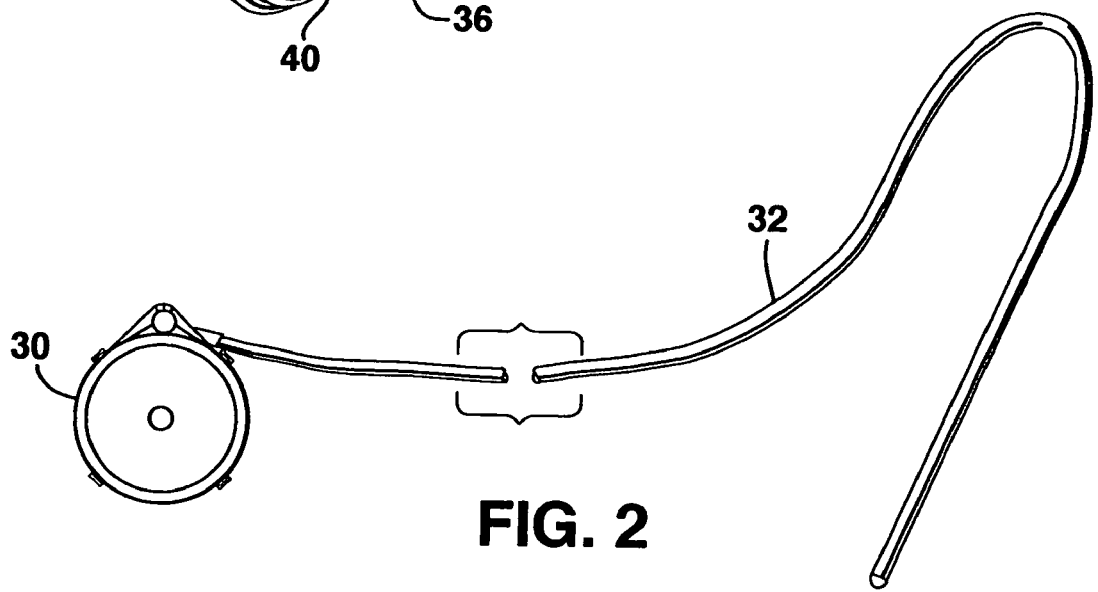
FIG. 2 shows an implantable therapeutic substance delivery device with catheter embodiment.

FIG. 1 shows the environment of an implantable medical device known as an implantable therapeutic substance delivery device 30, also known as a drug pump, having a permanent magnet solenoid pump embodiment. The therapeutic substance delivery device 30 can be used for a wide variety of therapies such as pain, spasticity, cancer, and many other medical conditions. The implantable therapeutic substance delivery device 30 is typically implanted by a clinician such as a surgeon in a sterile surgical procedure performed under local, regional, or general anesthesia. Before implanting the therapeutic substance delivery device 30, a catheter 32 is typically implanted with the distal end position at the desired therapeutic substance delivery site 34 and the proximal end tunneled to the location where the therapeutic substance delivery device 30 is to be implanted. The catheter 32 and the therapeutic substance delivery site 34 can generate a back pressure during infusion known as the infusion site pressure that the therapeutic substance delivery device 30 overcomes to deliver therapeutic substance 36 at the infusion site. The implantable therapeutic substance delivery device 30 is generally implanted subcutaneously about 2.5 cm (1.0 inch) beneath the skin where there is sufficient subcutaneous tissue to support the implanted system. Once the therapeutic substance delivery device 30 is subcutaneously implanted into the patent, the incision can be sutured closed and the therapeutic substance delivery device 30 can begin operation.

The therapeutic substance delivery device 30 operates to infuse a therapeutic substance 36 at a programmed rate into a patient 38. The therapeutic substance 36 is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance 36 can be replenished in some embodiments of the implanted therapeutic substance delivery device 30 by inserting a non-coring needle connected to a syringe filled with therapeutic substance 36 through the patient's skin into a septum 40 on the therapeutic substance delivery device 30 to fill the implanted device. If the therapeutic substance delivery device 30 requires replacement due to conditions such as battery depletion or other condition, an incision is made near the implanted therapeutic substance delivery device 30, and the old therapeutic substance delivery device 30 is removed, also known as explanted. After the old therapeutic substance delivery device 30 has been explanted, typically a new therapeutic substance delivery device 30 is then implanted.

Figure 3:
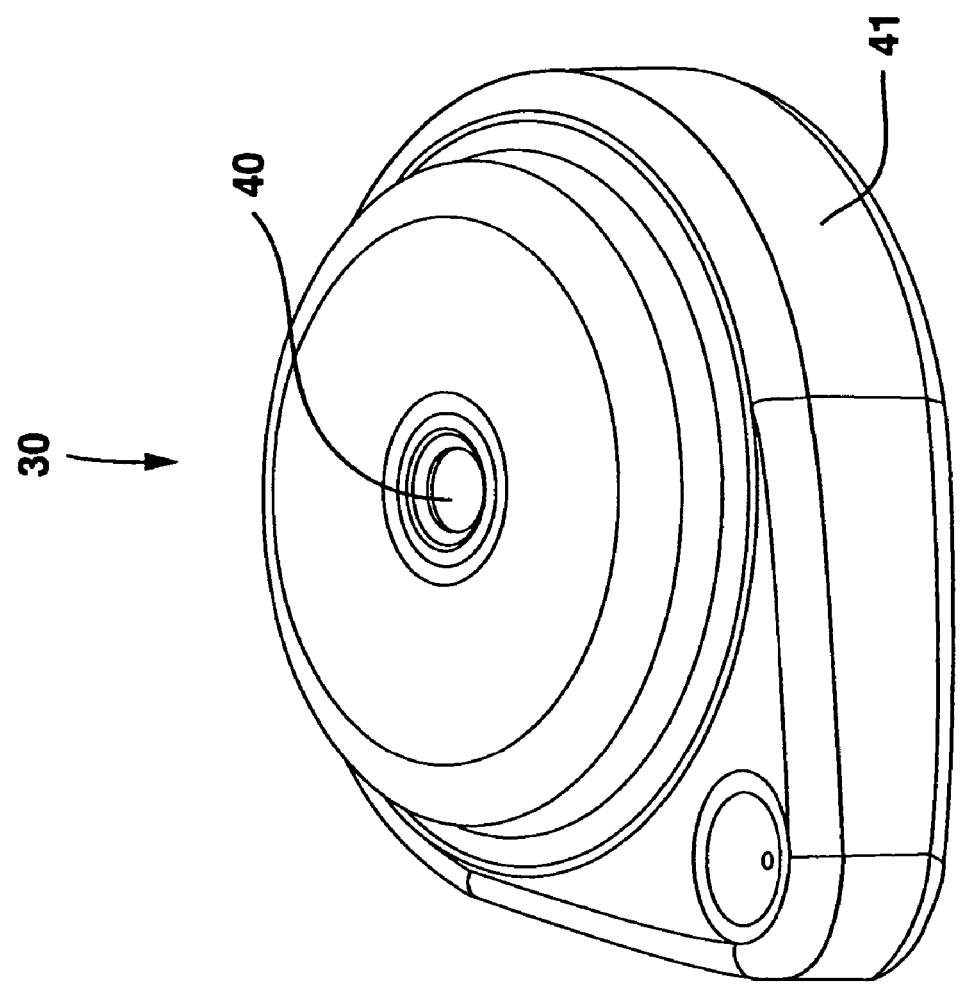
FIG. 3 shows an implantable therapeutic substance delivery device embodiment.
Figure 4:
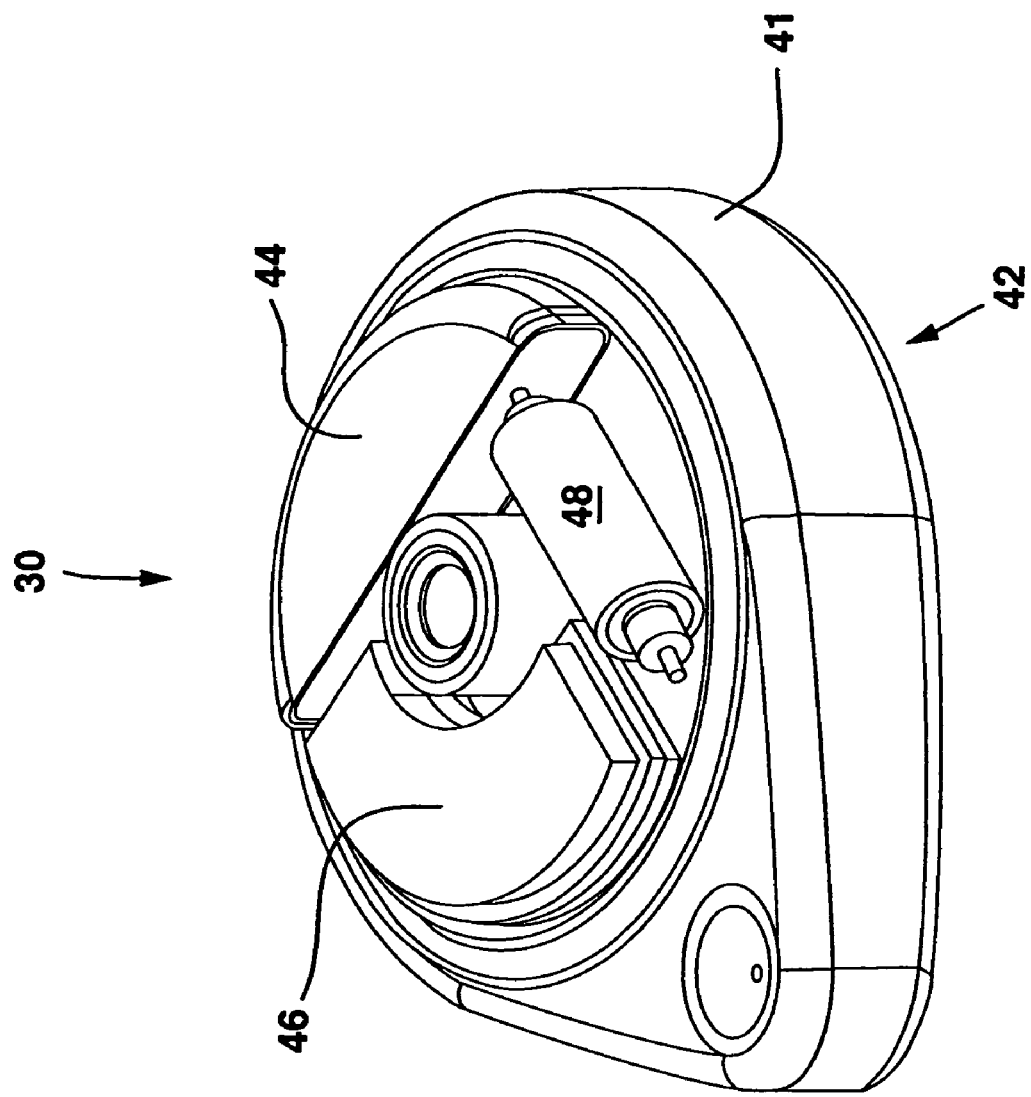
FIG. 4 shows the implantable therapeutic substance delivery device of FIG. 3 with a portion of a housing removed.
Figure 5:
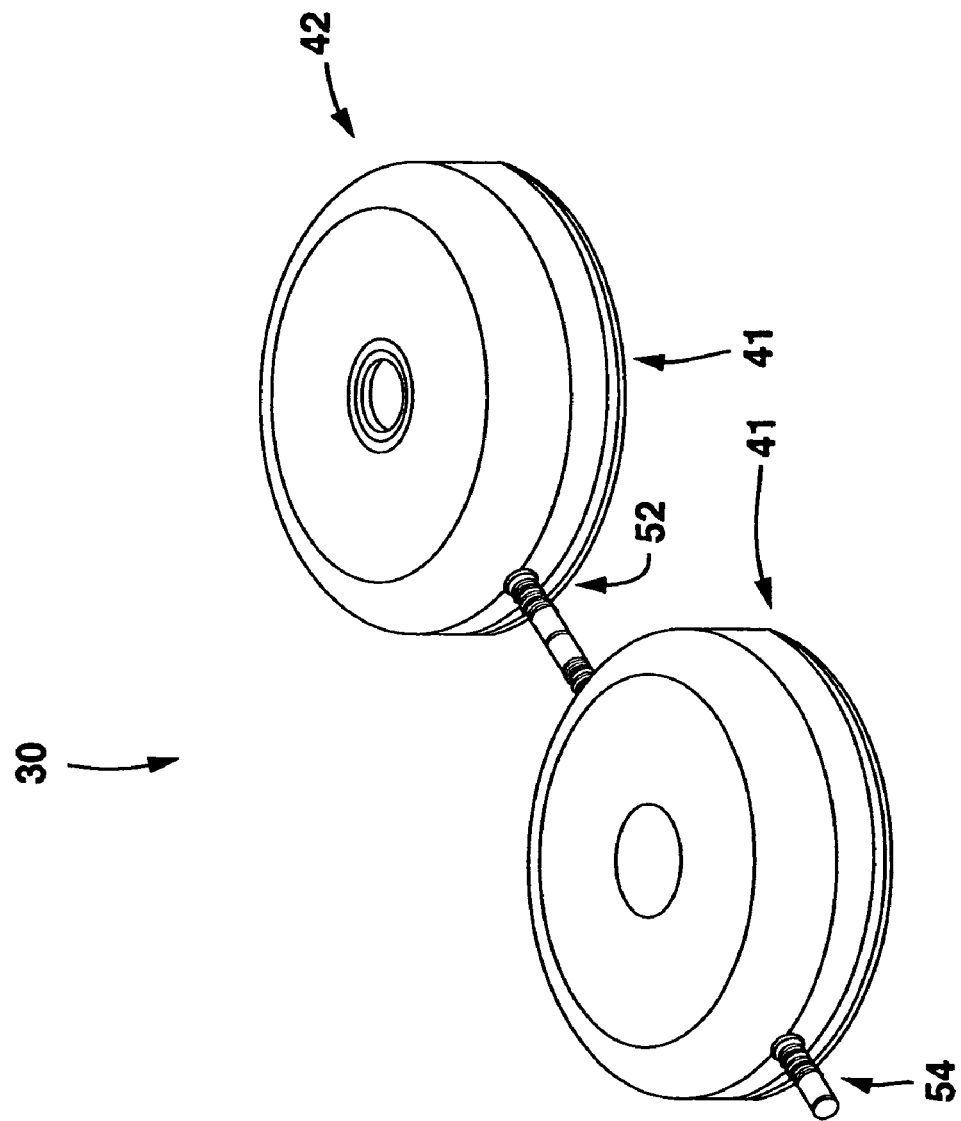
FIG. 5 shows another implantable therapeutic substance delivery device embodiment having a separate therapeutic substance reservoir.
Figure 6:
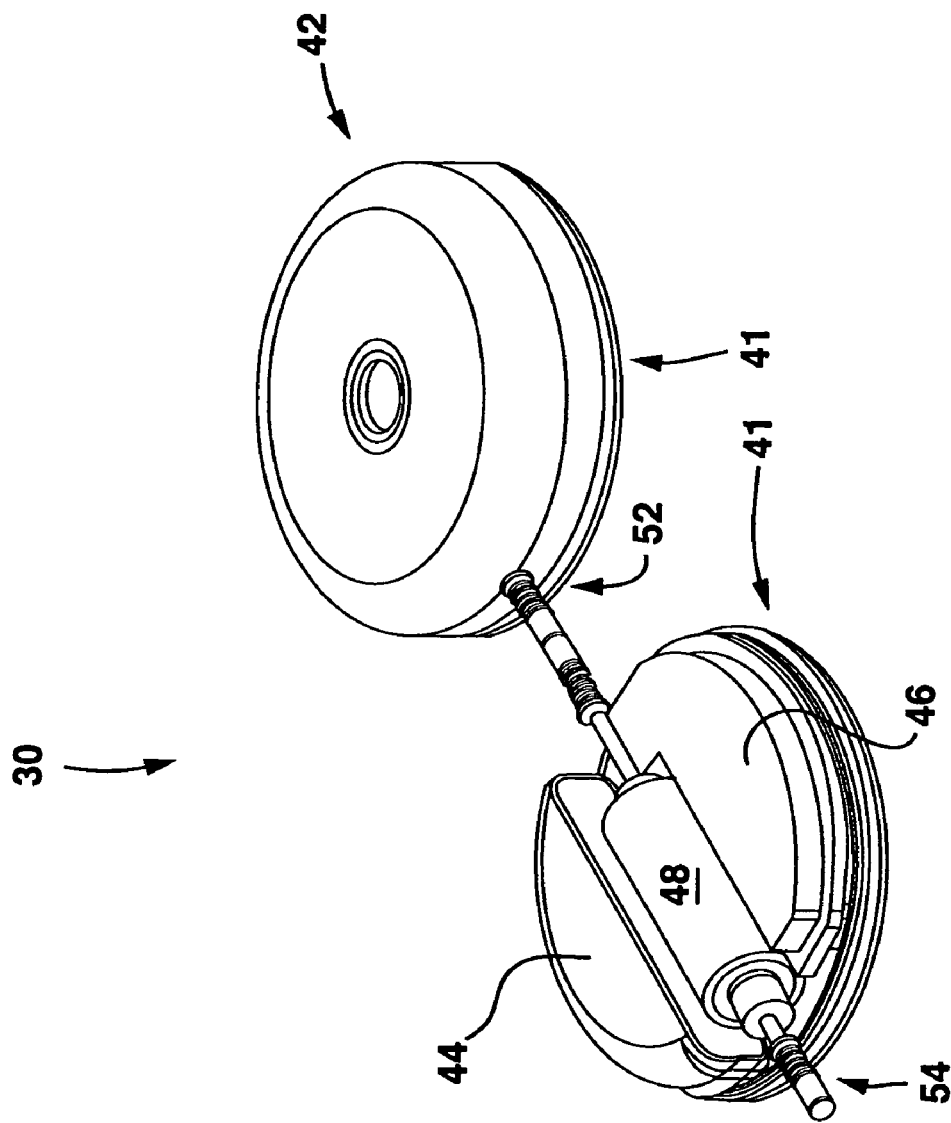
FIG. 6 shows the implantable therapeutic substance delivery device of FIG. 5 with a portion of a housing removed.
Figure 7:
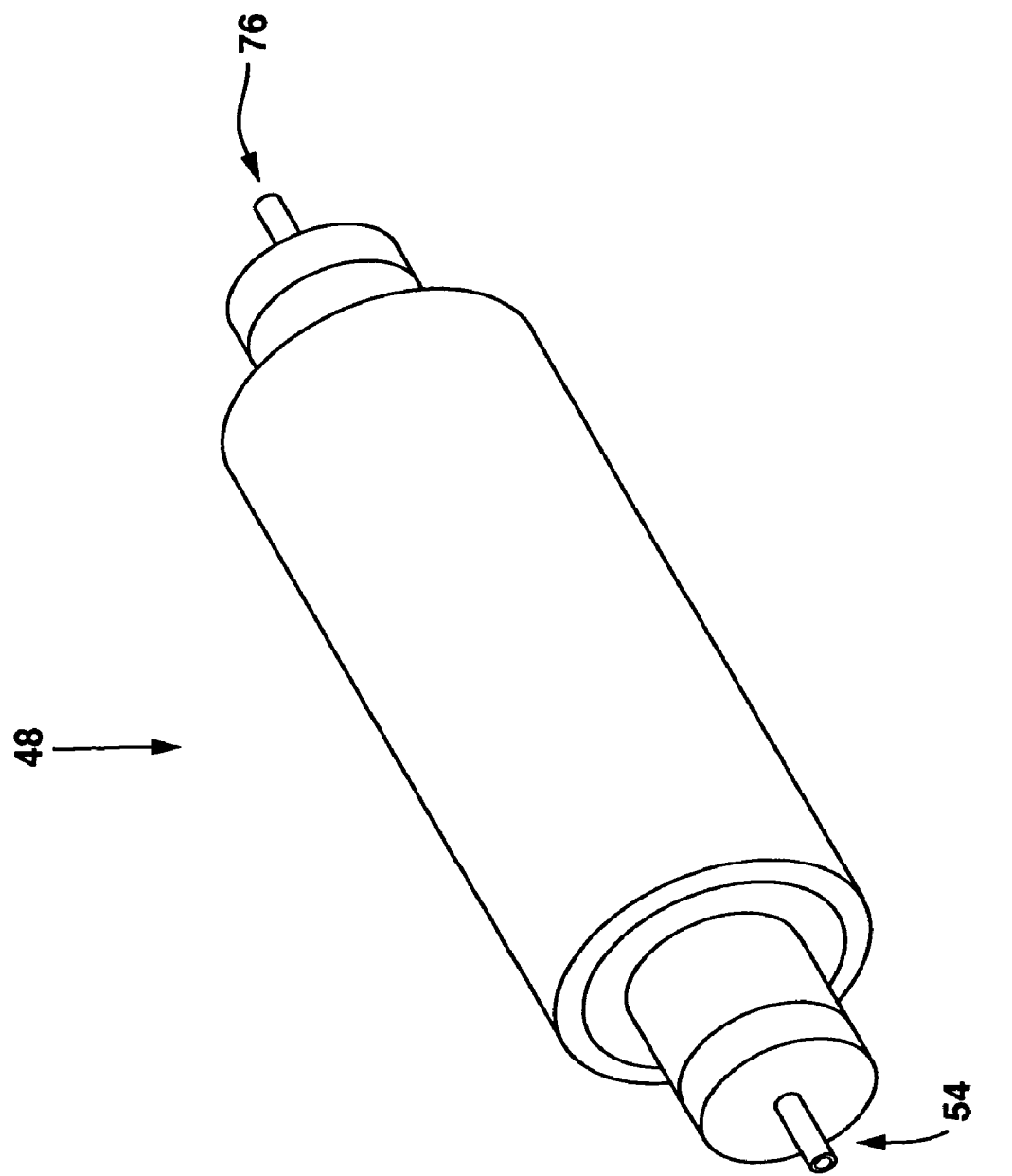
FIG. 7 shows a permanent magnet solenoid pump embodiment.
Figure 8:
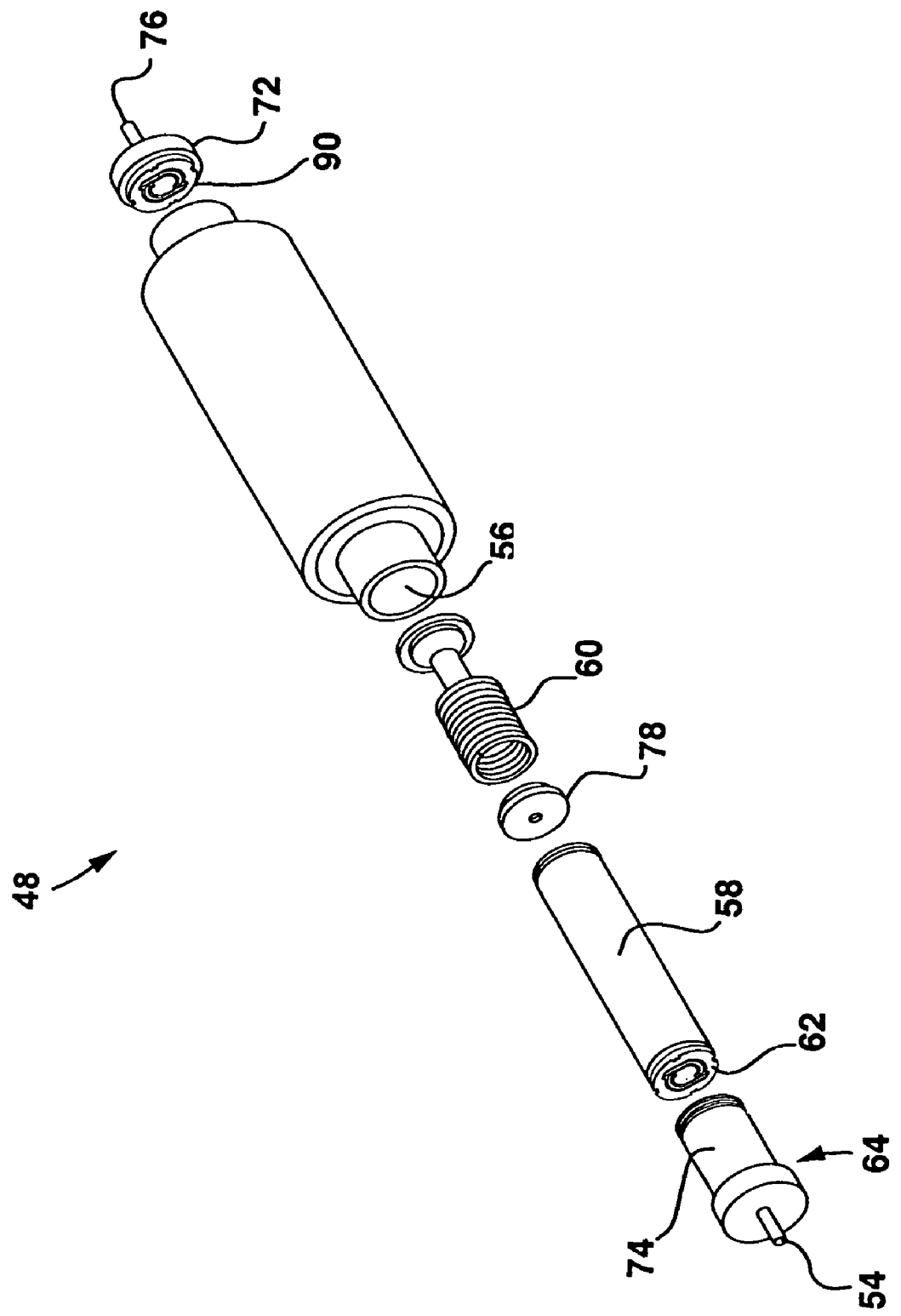
FIG. 8 shows an exploded view of the permanent magnet solenoid pump of FIG. 7 embodiment.
Figure 9:
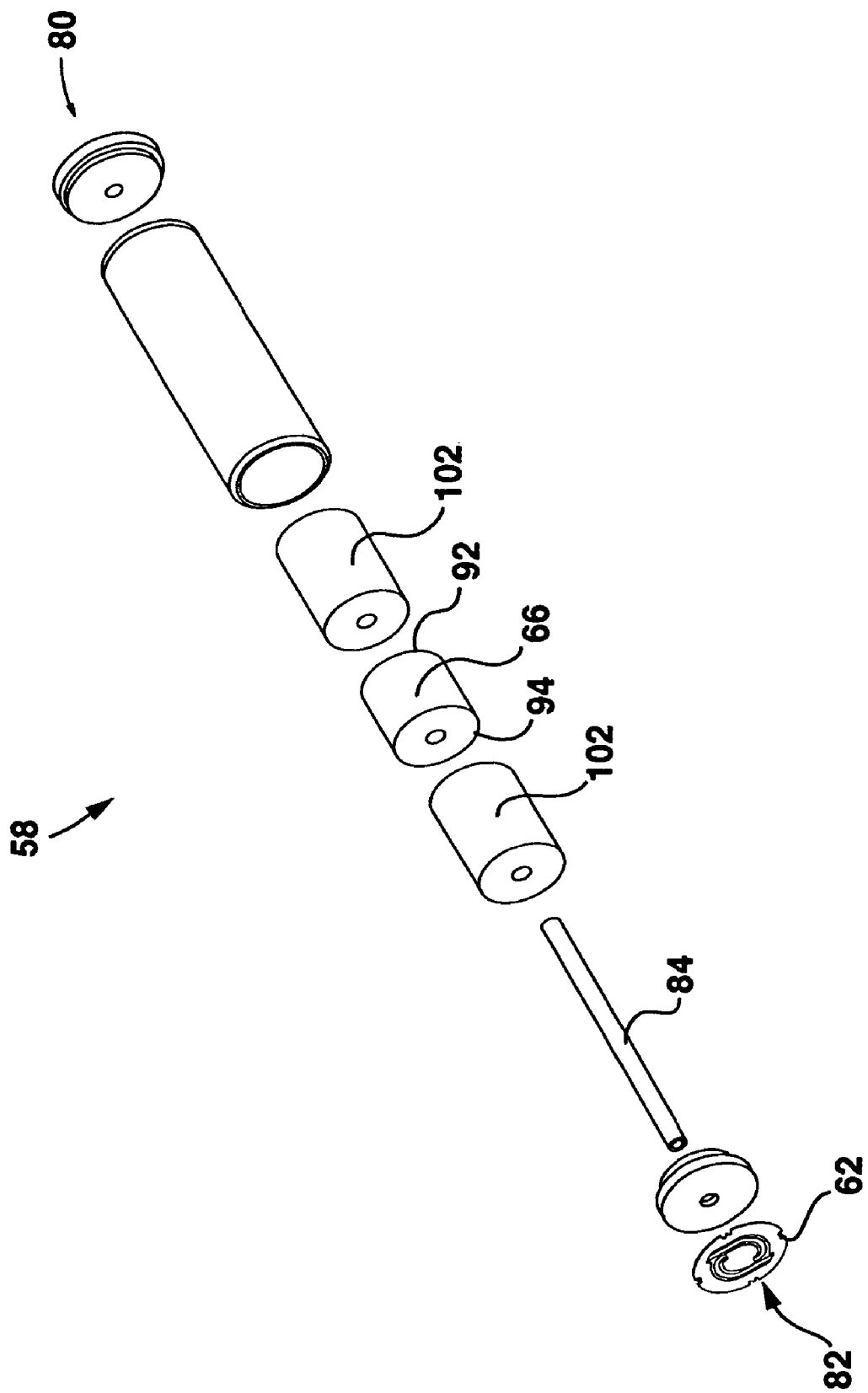
FIG. 9 shows an exploded view of a pump piston for a permanent magnet solenoid pump three-coil embodiment.
Figure 10:
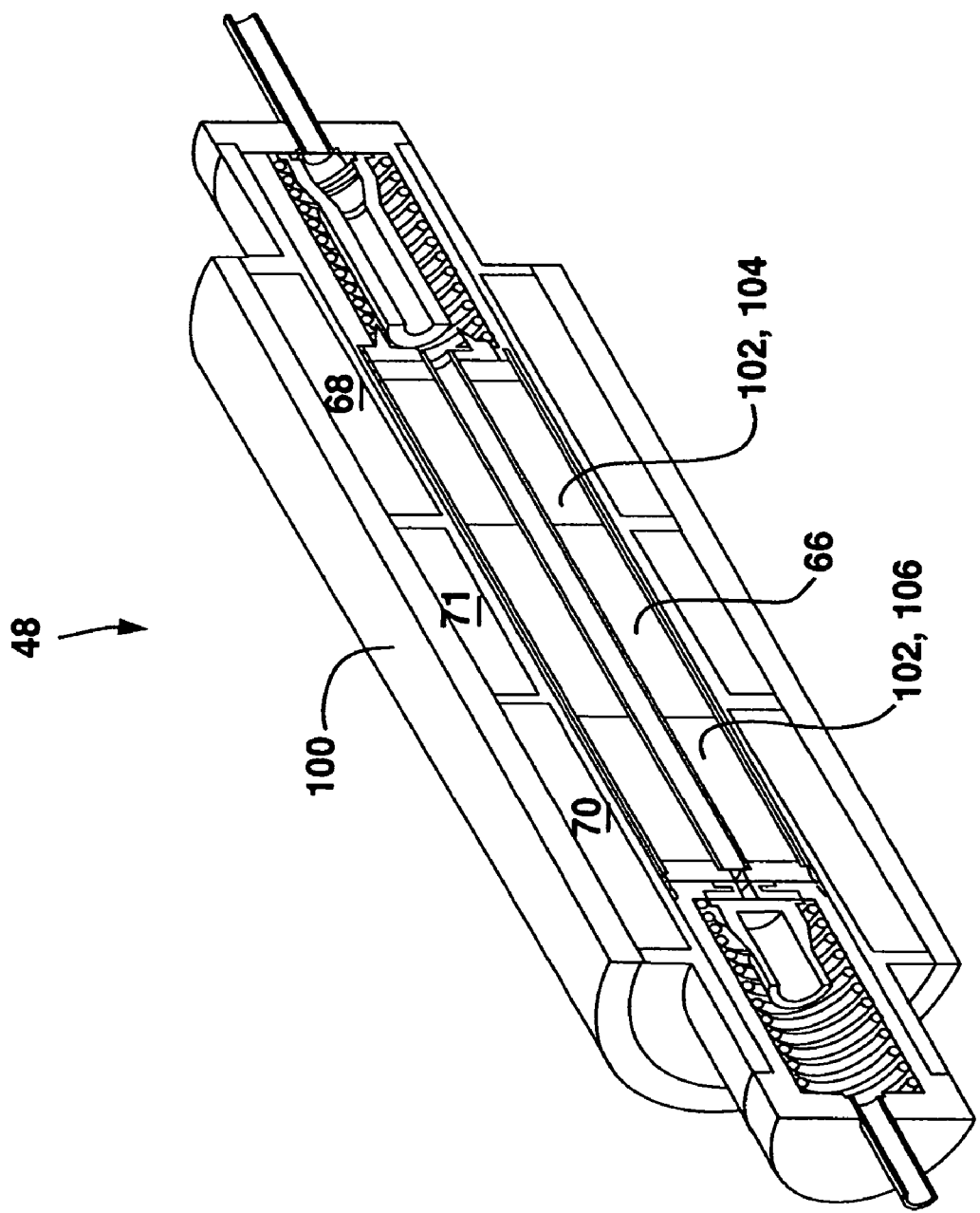
FIG. 10 shows an isometric cross-section view of a pump piston for a permanent magnet solenoid pump three-coil embodiment.
Figure 11:
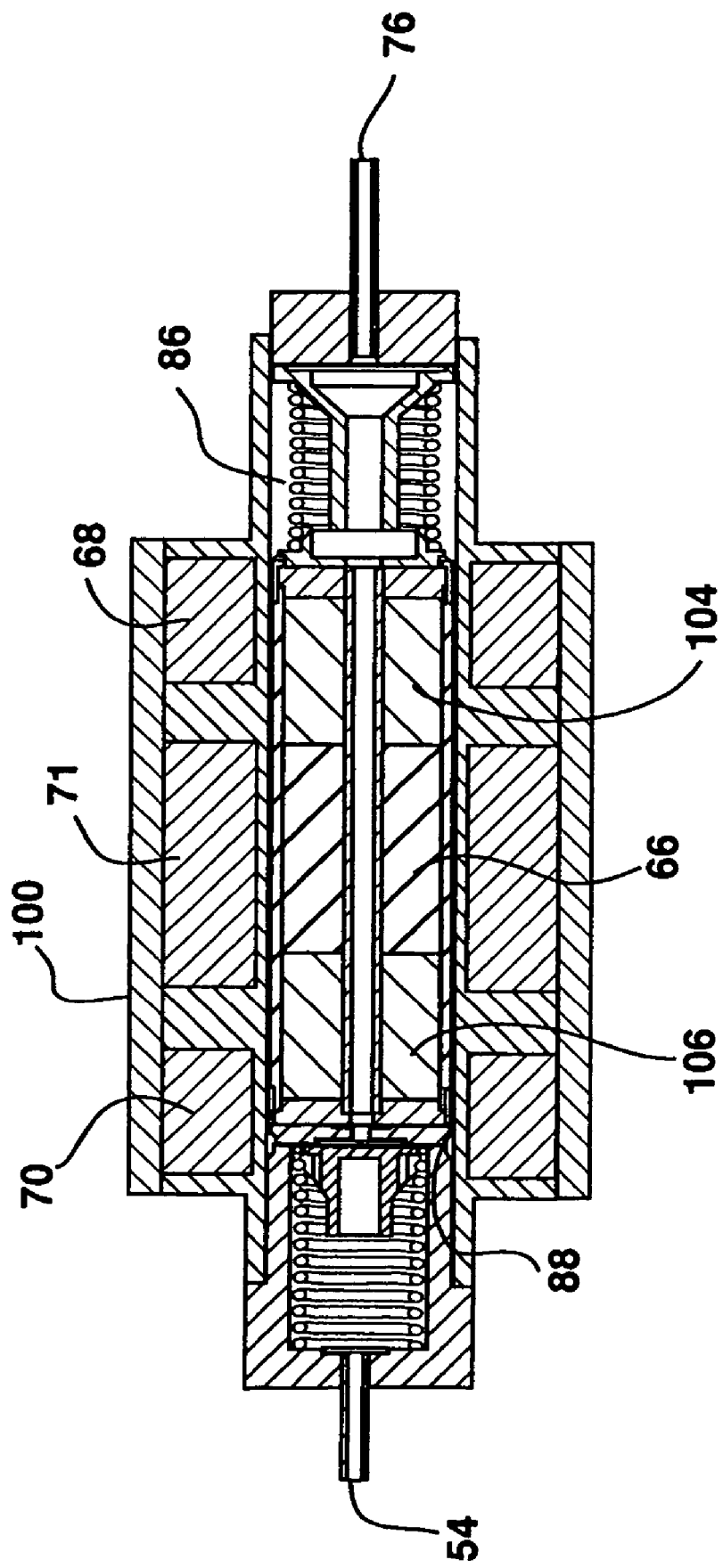
FIG. 11 shows a cross section view of a pump piston for a permanent magnet solenoid pump three-coil embodiment.

FIGS. 3-6 show views of therapeutic substance delivery device 30 embodiments. An implantable therapeutic substance delivery device 30 with a permanent magnet solenoid pump comprises a housing 41, a therapeutic substance reservoir 42, a power source 44, electronics 46, and a permanent magnet solenoid pump 48. Typically, the therapeutic substance delivery device 30 components are carried in a single housing 41, such as shown in FIGS. 3 and 4, that is manufactured from a material that is biocompatible and hermetically sealed such as titanium, tantalum, stainless steel, plastic, ceramic, and the like. Therapeutic substance delivery device 30 components can also be placed in more than one housing 41, such as shown in FIGS. 5 and 6, that are appropriately coupled. The therapeutic substance reservoir 42 can be placed inside the housing 41 or can be separated from the housing 41 with a fluid coupling such as a tube between the reservoir 41 and the housing 41. The therapeutic substance reservoir 42 is configured to contain a therapeutic substance 36 and may use geometries such as a metal bellows, polyomeric bag, and the like. The therapeutic substance reservoir 42 has a reservoir outlet 52 and can have a septum 40 for refilling the reservoir 42.

The power source 44 is carried in the housing 41. The power source 44 is selected to operate the solenoid pump 48 and electronics 46 such as a lithium ion (Li+) battery, capacitor, and the like. The electronics 46 are coupled to the power source 44 and typically include memory and a controller. The controller can be an Application Specific Integrated Circuit (ASIC) state machine, a gate array, or may include a microprocessor. The electronics 46 are configured to control the solenoid pump 48 infusion rate and can be configured to operate many other features such as patient alarms and the like. The electronics 46 can also include telemetry circuitry configured to receive and send information when the therapeutic substance delivery device 30 is implanted to allow programming of the infusion rate. The solenoid pump 48 is coupled to the electronics 46 and coupled to the therapeutic substance reservoir outlet 52 and configured for pumping therapeutic substance 36 from the therapeutic substance reservoir 42 through an infusion outlet 54 at a programmed rate.

FIGS. 7-11 show a three coil embodiment of the solenoid pump. The permanent magnet solenoid pump 48 comprises a pump cylinder 56, a pump piston 58, a biasing element 60, an inlet valve 62, an outlet valve 64, a permanent magnet 66, a first coil 68, and a second coil 70. The solenoid pump 48 is coupled to the electronics 46, the therapeutic substance reservoir outlet 52, and the infusion outlet 54. The solenoid pump 48 is configured for pumping therapeutic substance 36 from the reservoir 42 through an infusion outlet 54 at a programmed rate.

The pump cylinder 56 has an inlet enclosure 72, an outlet enclosure 74, a therapeutic substance inlet 76, and an infusion outlet 54. The inlet enclosure 72 transitions the pump cylinder 56 to the therapeutic substance inlet 76. The outlet enclosure 74 transitions the pump cylinder 56 to the infusion outlet 54. The therapeutic substance inlet 76 is coupled to a therapeutic substance reservoir outlet 52 and coupled to the inlet enclosure 72 on the pump cylinder 56. Some embodiments can include a piston seal 78 positioned between the pump cylinder 56 and the pump piston 58 to reduce therapeutic substance 36 flow between the pump piston 58 and the pump cylinder 56 and provide other functions. The piston seal 78 can be configured to serve as a guide for the biasing element 60 and to cushion the pump piston 58 at the end of pump piston 58 retraction for the intake stroke. The piston seal 78 is manufactured from a resilient material with good sealing qualities such as synthetic rubber, PTFE, silicone, and the like.

The pump piston 58 is moveable within the pump cylinder 56 and has a piston inlet end 80, a piston outlet end 82, and a piston fluid path 84. The pump piston 58 forms an inlet chamber 86 between the pump piston 58 and the inlet enclosure 72 and a pumping chamber 88 between the pump piston 58 and the outlet enclosure 74. The inlet chamber 86 contains the therapeutic substance 36 that is displaced when the pump piston 58 retracts. The pumping chamber 88 contains the therapeutic substance 36 that is displaced when the pump piston 58 is actuated. The piston fluid path 84 is configured to provide fluid communication between the inlet chamber 86 and the pumping chamber 88 that is controlled by the inlet valve 62. The piston fluid path 84 can take a wide variety of forms such as a central fluid path, a side fluid path, a partial central and partial side fluid path, and the like.

The biasing element 60 is positioned in the pump cylinder inlet chamber 86 between the pump piston 58 and the inlet enclosure 72. The biasing element 60 exerts force on the pump piston 58 to expulse therapeutic substance 36 through the infusion outlet 54. In some embodiments, the biasing element 60 exerts substantially the sole force on the pump piston 58 to expulse therapeutic substance 36 through the infusion outlet 54. The biasing element 60 also provides force to maintain the pump piston 58 in an actuated position until retracted to seal the inlet valve 62 against the outlet enclosure 74 to provide redundant protection against unintended flow of therapeutic substance 36 to the patient 38. The biasing element 60 can be one or more of a wide variety of biasing structures that are selected to provide the desired biasing force on the pump piston 58. The desired force of the biasing element 60 in a particular embodiment is the force required to overcome any frictional losses during the pump piston 58 expulsion stroke, to generate pressure to open the outlet valve 64, and to overcome pressure losses between the infusion outlet 54 and the infusion site 34 that can be located at the distal end of the catheter 32. Some specific embodiments of the biasing element 60 include a spring, a coil spring, and the like.

Figure 15:
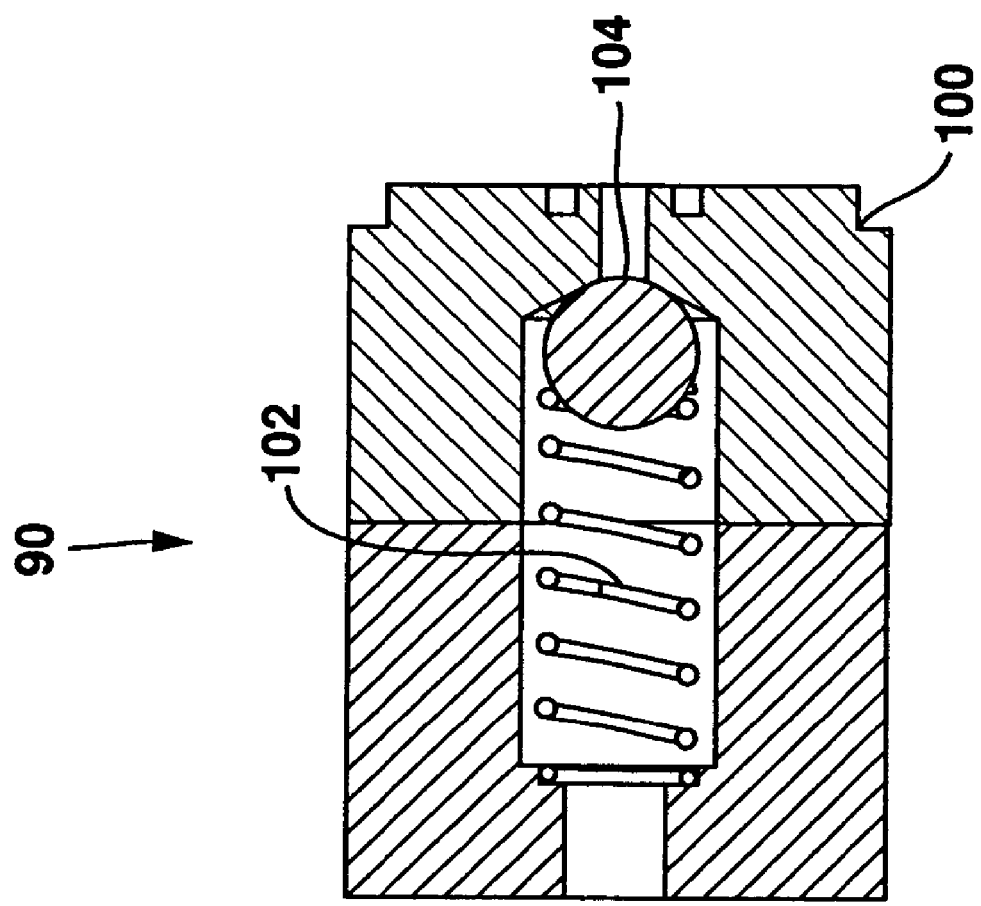
FIG. 15 shows an outlet valve embodiment.
Figure 16:
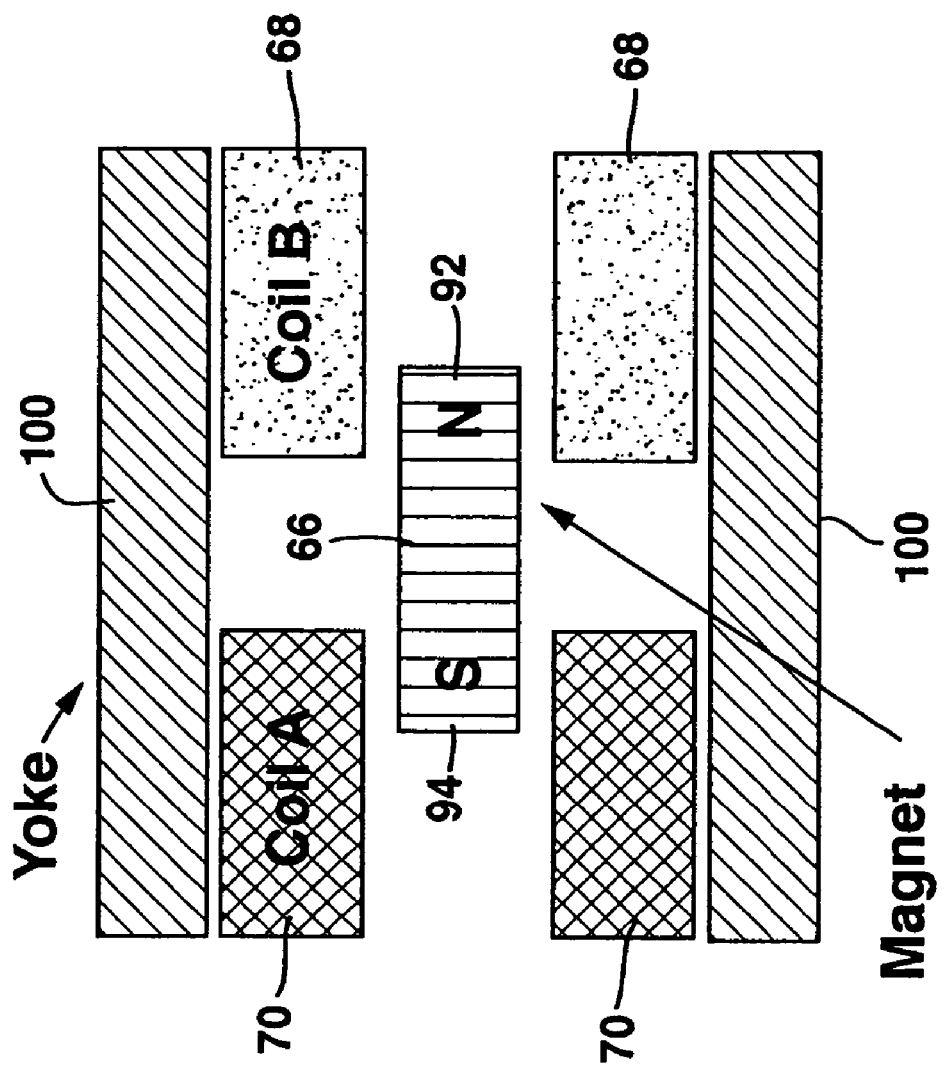
FIG. 16 shows a schematic of a two-coil permanent magnet solenoid pump embodiment.
Figure 17:
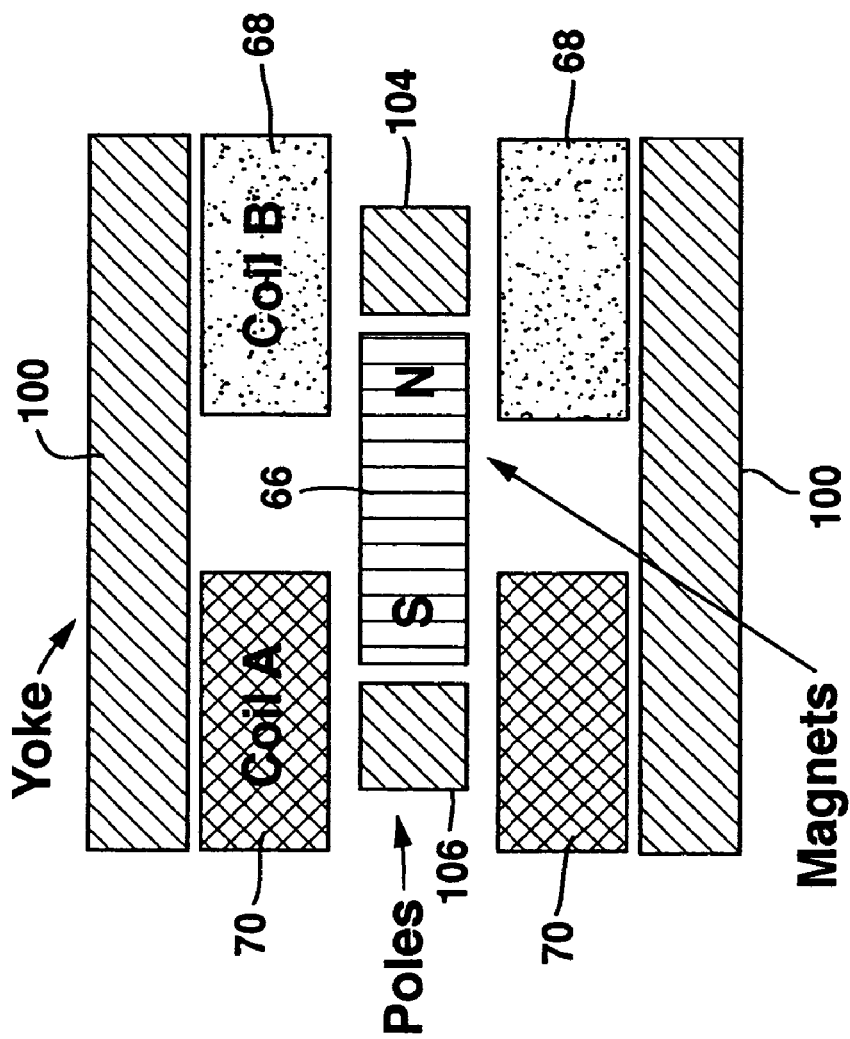
FIG. 17 shows a schematic of a two-coil with permanent magnet pole pieces permanent magnet solenoid pump embodiment.
Figure 18:
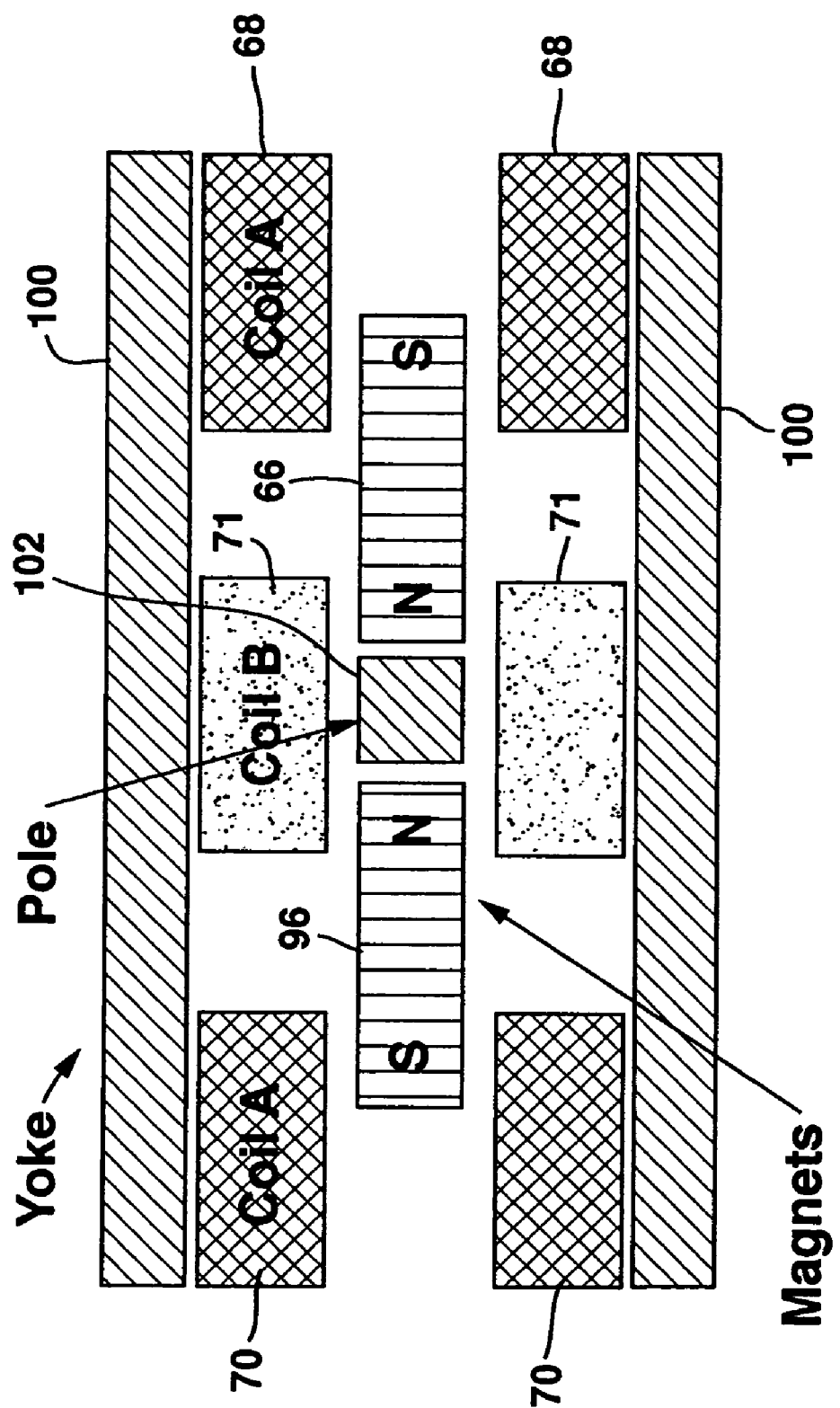
FIG. 18 shows a schematic of a three-coil permanent magnet solenoid pump embodiment.
Figure 19:
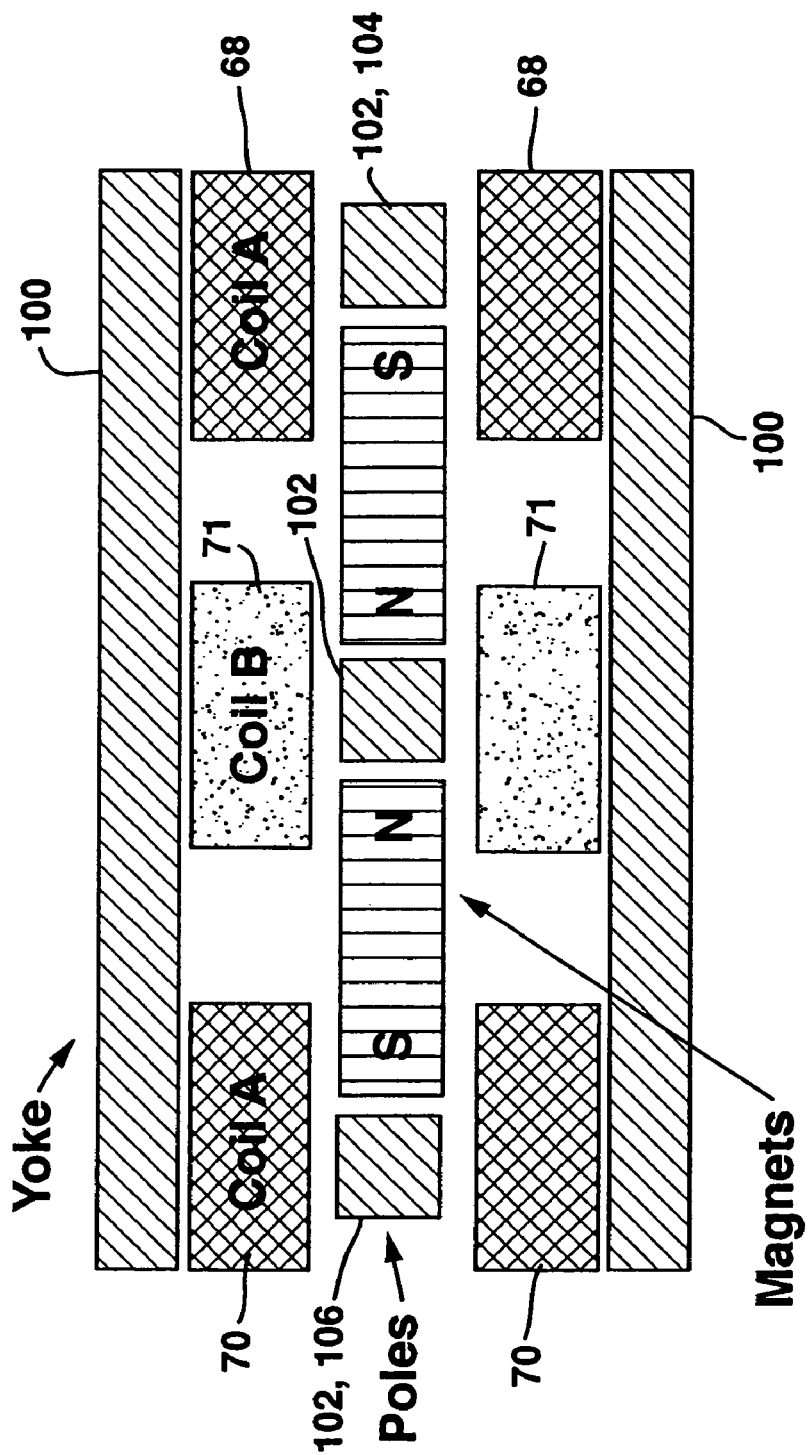
FIG. 19 shows a schematic of a three-coil with permanent magnet pole pieces permanent magnet solenoid pump embodiment; and, FIG. 20 shows a flow diagram of a method for operating a permanent magnet solenoid therapeutic substance delivery device embodiment.

The inlet valve 62 is carried on the pump piston outlet end 82. The inlet valve 62 can be a variety of inlet valves 62 such as a flapper valve, annular flapper valve, ball valve, reed valve, duckbill valve, poppet valve, and the like. The outlet valve 64 is carried in the outlet enclosure 74 and coupled to the infusion outlet 54. The outlet valve 64 improves solenoid pump 48 safety by substantially preventing unintended flow of therapeutic substance 36 when the reservoir 42 pressure is greater than the infusion site 34 pressure. The outlet valve 64 improves solenoid pump 48 accuracy by maintaining sufficient back pressure to keep the inlet valve 62 closed during therapeutic substance 36 expulsion through the infusion outlet 54 so that addition therapeutic substance 36 is not infused when the reservoir 42 pressure is greater than the infusion site 34 pressure. The outlet valve 64 can be a variety of outlet valves 64 such as a flapper valve, ball valve, reed valve, duckbill valve, poppet valve, and the like. An outlet valve embodiment is shown in FIG. 15.

Some embodiments of the solenoid pump 48 can include an anti-cavitation valve 90 position in fluid communication with the therapeutic substance inlet 76. The anti-cavitation valve 90 substantially prevents therapeutic substance 36 in the inlet chamber 86 from flowing back through the therapeutic substance inlet 76 during pump piston 58 retraction. Since the therapeutic substance 36 cannot flow backwards, pressure in the inlet chamber 86 increases as the pump piston 58 retracts causing the therapeutic substance 36 to flow through the piston fluid path 84 without causing the pump chamber 88 pressure to drop low enough to cause dissolved gasses to come out of solution. Also by substantially preventing the back flow of therapeutic substance 36 through the therapeutic substance inlet 76 during pump piston 58 retraction, piston pump 58 efficiency is improved because wasted therapeutic substance 36 flow is minimized. The anti-cavitation valve 90 can be a wide variety of anti-cavitation valves 90 such as a flapper valve, annual flapper valve, ball valve, reed valve, duckbill valve, poppet valve, and the like. In addition to displacing therapeutic substance 36 that operates the inlet valve 62, outlet valve 64, and anti-cavitation valve 90, the pump piston 58 carries a permanent magnet 66.

Figure 12:
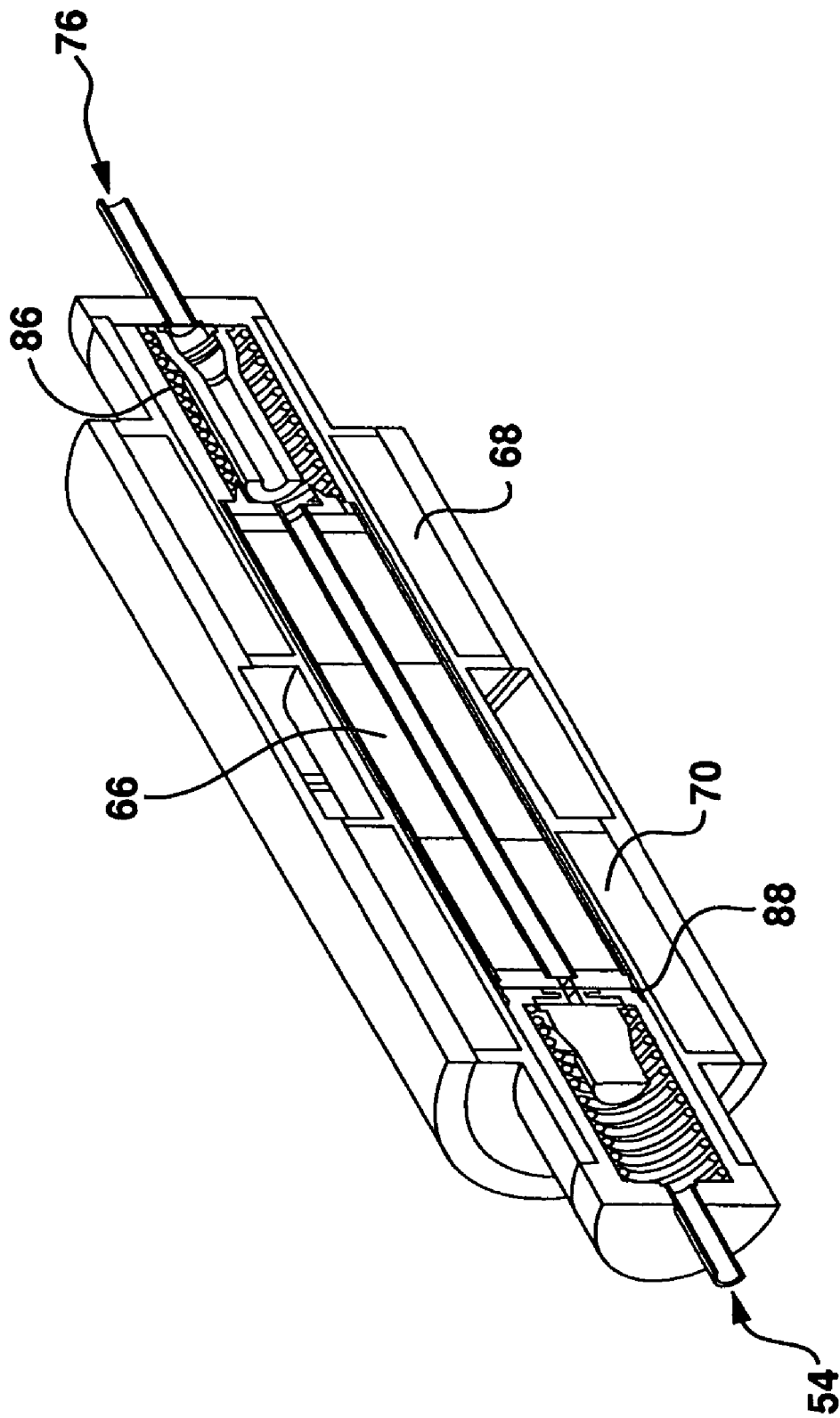
FIG. 12 shows an isometric cross-section view of a permanent magnet solenoid pump two-coil embodiment.
Figure 13:
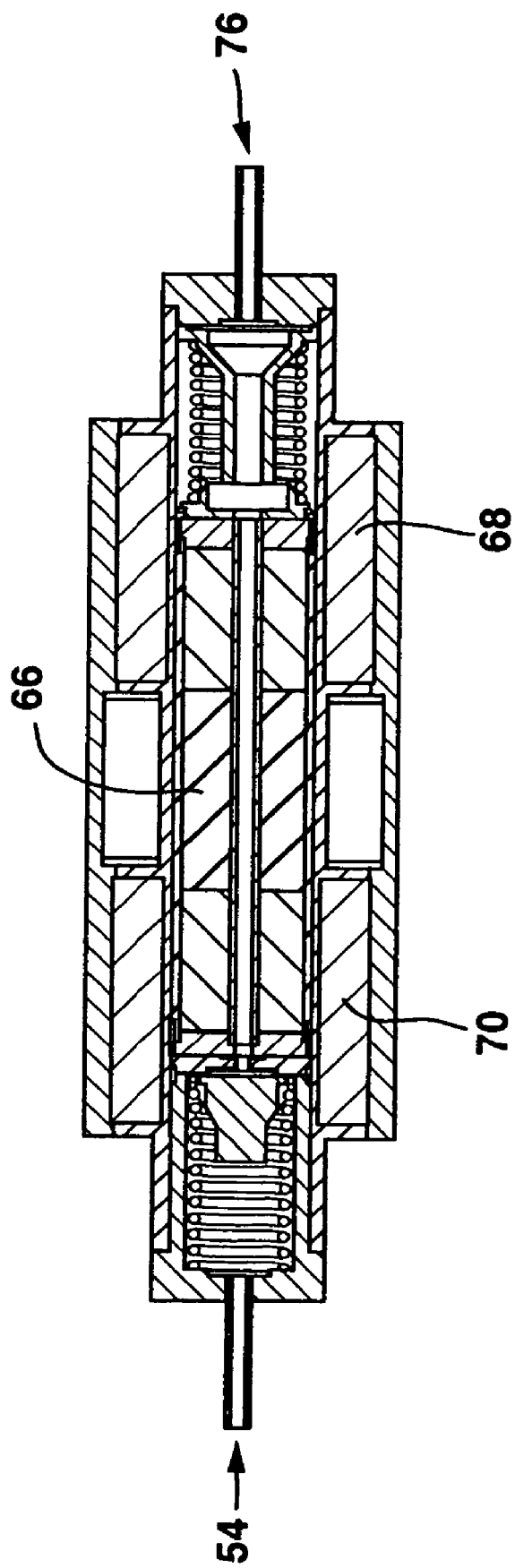
FIG. 13 shows a cross section view of a permanent magnet solenoid pump two-coil embodiment.
Figure 14B:
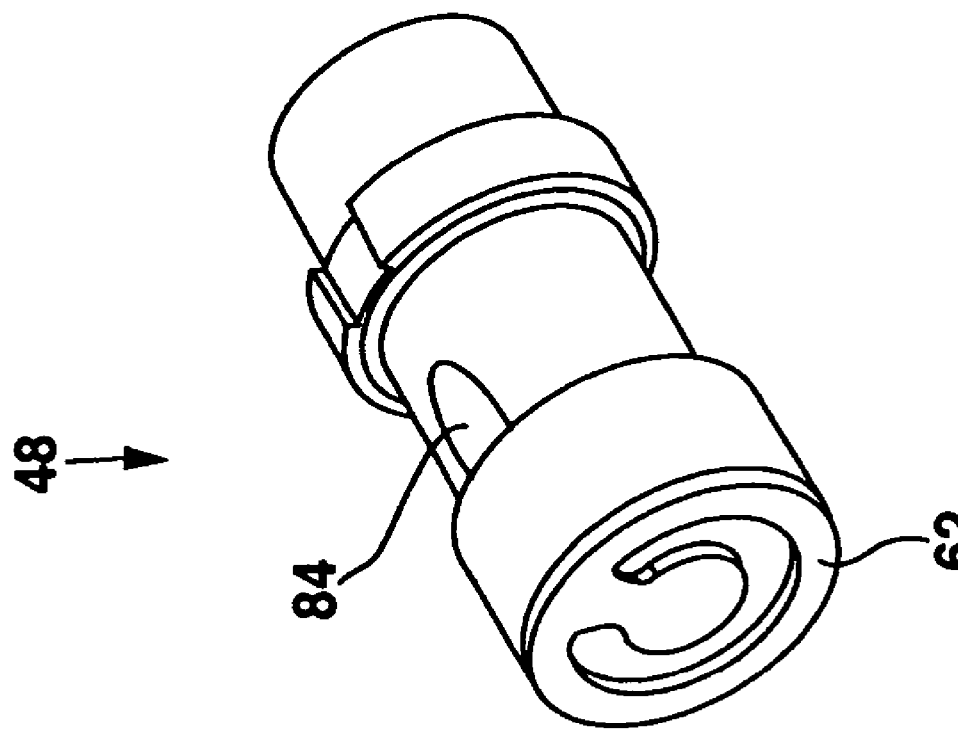
FIGS. 14a and 14b show a pump piston with an alternative piston fluid path embodiments.
Figure 14A:
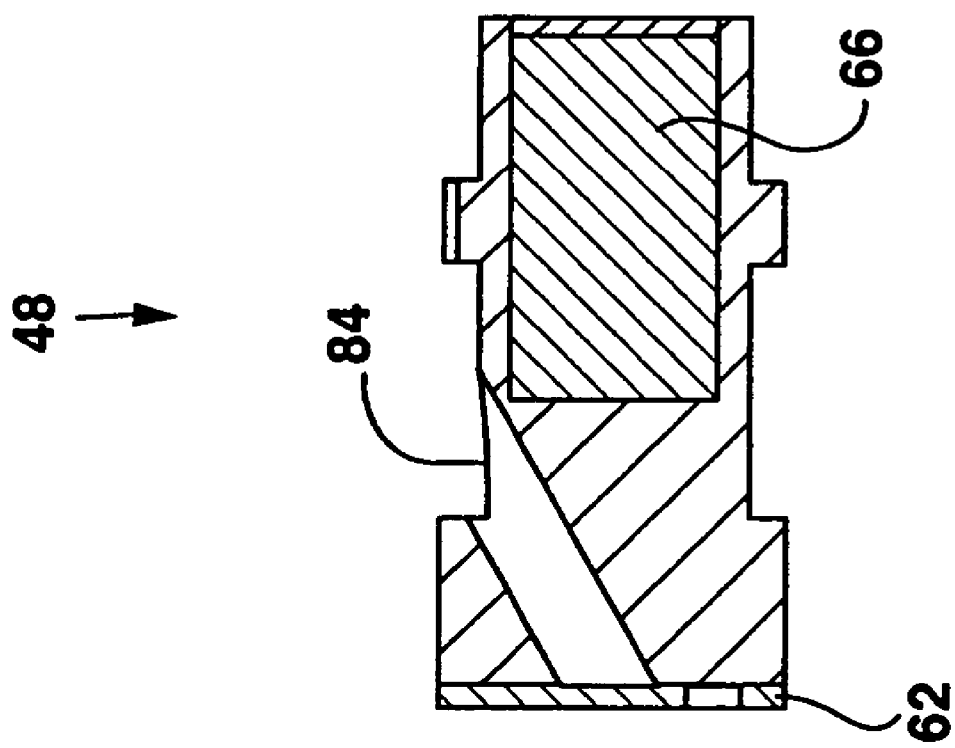

The permanent magnet 66 is at least a first permanent magnet 66 having a first pole 92 and a second pole 94. The permanent magnet 66 is carried by the pump piston 58 and acted on by the magnetic fields created by the coils 67 that include at least the first coil 68 and at least the second coil 70. When the first coil 68 and second coil 70 are energized, the coils 67 produce an electromagnetic axial force that acts on the permanent magnet 66 to impart motion to the pump piston 58. In some embodiments, there can be more than one permanent magnet 66 such as a first permanent magnet 66, a second permanent magnet 96, a third permanent magnet 98 and so forth. Also in some embodiments, there can be more than a first coil 68 and second coil 70 such as a third coil 71 and so fourth. When using more than one permanent magnet 66, like poles are positioned adjacent to one another, and there are N−1 operational permanent magnets 66 where N is the number of coils 67 in the range from about 3 to 10. The permanent magnet 66 is manufactured from a hard ferromagnetic material such as samarium cobalt, neodymium, ceramic, alnico, and the like. Since the permanent magnet 66 material is typically not therapeutic substance compatible or biocompatible, the permanent magnet 66 is typically isolated from the therapeutic substance 36 by the piston fluid path 84 and the pump piston 58 sealed is by the piston inlet end 80 and piston outlet end 82. Positioned in operating relationship to the permanent magnet 66 are the first coil 68 and the second coil 70. An alternative solenoid pump 48 embodiment using two coils 67 is shown in FIGS. 12-13.

FIGS. 16-19 show block diagram of some of the permanent magnet solenoid pump 48 permanent magnet 66 and coil 67 embodiments. There is at least a first coil 68 configured around the pump cylinder 56 positioned adjacent to the first pole 92 of the permanent magnet 66, and at least a second coil 70 configured around the pump cylinder 56 positioned adjacent to the second pole 94 of the permanent magnet 66. The first coil 68 and the second coil 70 can be reversed in relation to the permanent magnet 66, so the first coil 68 is adjacent to the second pole 94 and the second coil 70 is adjacent to the first pole 92. Other embodiments of the permanent magnet solenoid pump 48 can have more than a first coil 68 and second coil 70 such as a third coil 71 or N operational coils where N is an integer in the range from about 3 to 10. When the solenoid pump 48 is configured with N coils there will be N−1 operational permanent magnets 66. The following discussion will use the term coil 67 to refer a first coil 68 and a second coil 70, or N coils and permanent magnet 66 to refer to a first permanent magnet 66 or N−1 permanent magnets.

The coils 67 are typically wound in opposite directions, so current flows in opposite directions to generate opposing magnetic fields. Alternatively, the coils 67 can be wound in the same direction and the voltage polarity applied to the coils 67 can be opposing to cause current to flow in opposite directions to generate opposing magnetic fields. The coils 67 are configured to create a force in one direction for one permanent magnet pole 92 and in the same direction for the other permanent magnet pole 94. The coils 67 are energized for pump piston 58 retraction toward the inlet enclosure 72 to fill the pump chamber 88 from the inlet chamber 86. Since the coils 67 are not typically compatible with therapeutic substances or biocompatible, the coils 67 are typically isolated from the therapeutic substance 36 by the pump cylinder 56 and isolated from the patient 38 by the housing 41. The pump cylinder 56 is manufactured from any therapeutic substance compatible material that meets design requirements such as titanium, tantalum, stainless steel, plastic, ceramic, and the like. The permanent magnet 66 and coils 67 can be inserted into the pump cylinder 56 along with the pump piston 58 and then the inlet enclosure 72 and outlet enclosures 74 can be welded to isolate the permanent magnet 66 and coils 67 from the therapeutic substance 36. The coil's 67 electromagnetic axial force can be enhanced with a magnetically permeable yoke 100 and pole pieces 102.

The magnetically permeable yoke 100 and pole pieces 102, although not required for operation, enhance the electromagnetic axial force created by the coils 67. The magnetically permeable yoke 100 is placed around the coils 67 to improve magnetic efficiency. The magnetically permeable yoke 100 also shields the permanent magnet 66 from external high magnetic fields, until the magnetically permeable yoke 100 becomes saturated, to protect the permanent magnet 66 from demagnetization. The external high magnetic field can be created by equipment such as Magnetic Resonance Imaging (MRI) equipment, magnetic security equipment, and the like. The pole pieces 102 can be positioned adjacent to one or more of the permanent magnet's 66 poles. For example, a first pole piece 104 can be carried on the pump piston 58 between the permanent magnet 66 and the inlet enclosure 72 to improve magnetic coupling. A second pole piece 106 can be carried on the pump piston 58 between the permanent magnet 66 and the outlet enclosure 74 to improve magnetic coupling.

When the pump piston 58 is fully positioned toward the inlet enclosure 72, the maximum pump chamber 88 volume is created. The pump chamber 88 has a pump chamber 88 volume comprising a stroke volume and a dead volume. The stroke volume is in the range from about 0.5 micro liters to about 5.0 micro liters. The sum of an inlet valve 62 opening pressure and the outlet valve 64 opening pressure exceeds the maximum pressure of the reservoir 42 less the infusion site 34 pressure to substantially prevent free flow of therapeutic substance 36 to the patient 38. The dead volume is less than half the stroke volume in the range from about 0.25 micro liters to about 2.5 micro liters. The solenoid pump's 48 small dead volume compared to the stroke volume improves the solenoid pump's 48 capability to pass air because of the low vacuum pressure that is typically generated in the pump chamber 88. The inlet valve 62 and outlet valve 64 opening pressures are selected to prevent unintended infusion under extreme operating conditions. Unintended infusion is substantially prevented by selecting the inlet valve 62 opening pressure and the outlet valve 64 opening pressure so the sum of these pressures is greater than the maximum pressure difference between the reservoir 42 and the infusion site 34. For example, unintended infusion is prevented when the reservoir 42 pressure is high and the ambient pressure (typically the same as the infusion site 34 pressure) is low that can occur when the reservoir 42 is full and the patient 38 is exposed to high temperature at high altitude.

The solenoid pump's 48 ability to pass air and operate accurately is a function of the solenoid pump's 48 compression ratio, the reservoir outlet 52 pressure, the infusion outlet 54 pressure, and outlet valve 64 cracking (opening) pressure. For adiabatic systems with ideal gases, the compression ratio in the pump chamber 88 can be expressed as $$CR_{pc} = \frac{V_{pc\,final}}{V_{pc\,initial}}$$

(Equation 1) where $CR_{pc}$ is the compression ratio in the pump chamber 88, $V_{pc\,final}$ is the final volume in the pump chamber 88 calculated by (stroke volume+pump chamber dead volume) where stroke volume=piston area×piston stroke, and $V_{pc\,initial}$ is the initial volume in the pump chamber 88 also known as the pump chamber dead volume which is also the pump chamber volume remaining after the pump piston 58 has expulsed the stroke volume. The compression ratio in the inlet chamber 86 can be expressed as $$CR_{ic} = \frac{V_{ic\,final}}{V_{ic\,initial}}$$

(Equation 2) where $CR_{ic}$ is the compression ratio in the inlet chamber 86 and $V_{ic}$ is the volume in the inlet chamber 86, $V_{ic\,final}$=(stroke volume+inlet chamber dead volume), and $V_{ic\,initial}$=(inlet chamber dead volume). From these relationships, it is apparent that pump chamber 88 pressure will be decreasing and inlet chamber 86 pressure will be increasing as the pump piston 58 retracts. For therapeutic substance 36 to flow into the pump chamber 88 when gas bubbles are present, the pressure in the pump chamber 88 during the pump piston 58 stroke must drop substantially below the inlet chamber 86 pressure. For therapeutic substance 36 to flow out of the pump chamber 88, the expulsion pressure must be greater than the infusion outlet 54 pressure. Therapeutic substance 36 flows through the outlet valve 64 when $P_{pc} \geq P_a + P_{ovc}$, where $P_{pc}$ is the pressure in the pump chamber 88, $P_a$ is the ambient pressure at the infusion outlet 54, and $P_{ovc}$ is outlet valve 64 cracking (opening) pressure. By selecting the appropriate outlet valve 64 cracking pressure the risk of unintentional infusion can be substantially eliminated.

The permanent magnet solenoid pump 48 is designed to be energy efficient consuming less than about 3.0 Joules per milliliter (J/ml) at about 137,895 pascals (20 pounds/square inch) back pressure. The solenoid pump 48 is about 5% to 10% efficient in terms of electrical energy input and fluid work output. The energy efficiency of the solenoid pump 48 to a large degree determines energy efficiency of the implantable therapeutic substance delivery device 30 and the size of power source 44 needed. For example, doubling solenoid pump 48 efficiency can theoretically result in nearly a 50% reduction in energy consumption and a 50% reduction in power source 44 size. Additionally, the solenoid pump 48 can be a wide variety of sizes. The design of the solenoid pump 48 permits small sized configuration such as less than about 20.0 mm long by about 6.0 mm in diameter with a total volume less than about 0.5 cc. The small size of the solenoid pump 48 also permit having a small implantable therapeutic substance delivery device 30 that can be implanted in a wide variety of location such as the head, arms, and legs.

Operation

Figure 20:
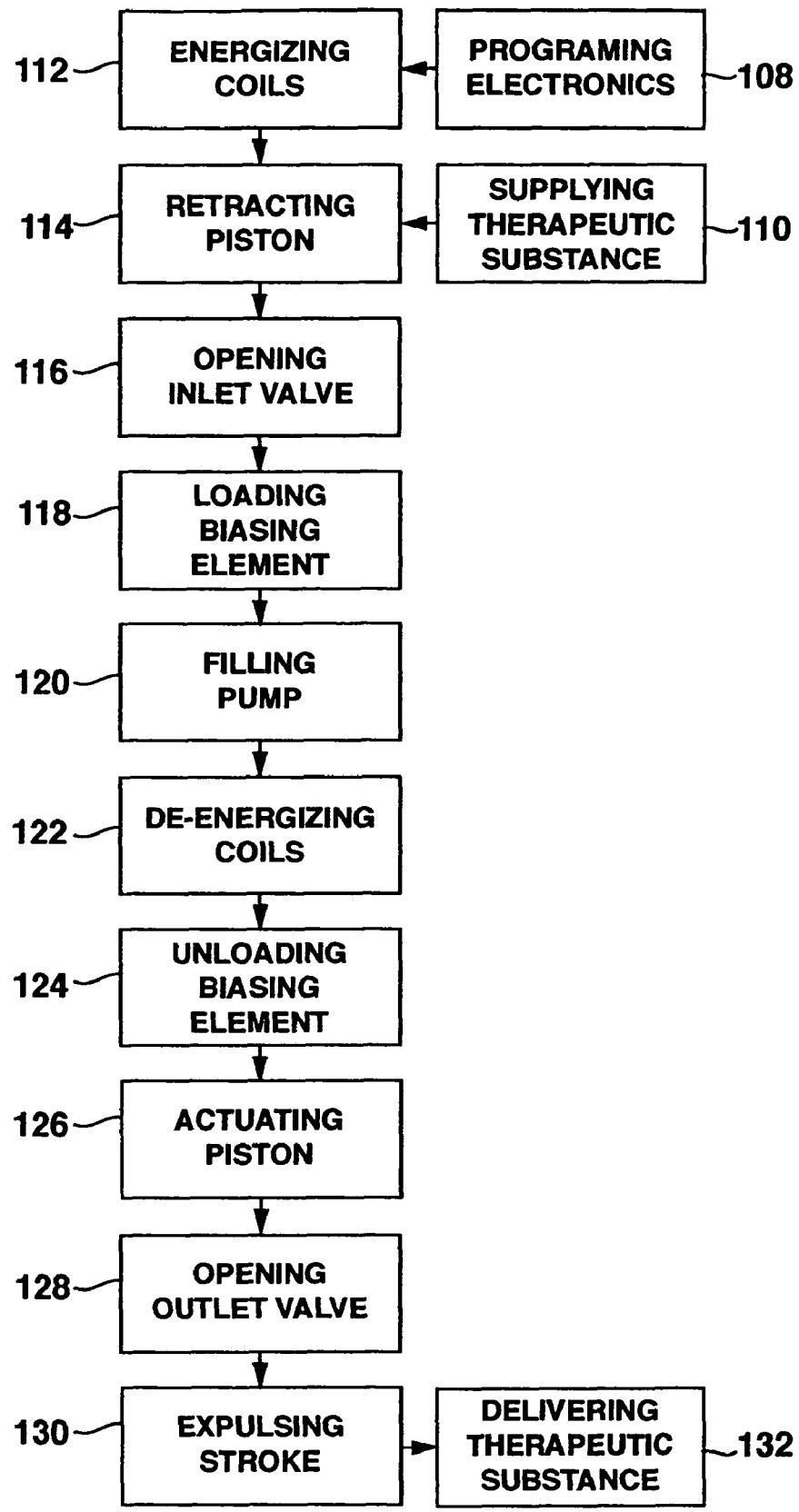

FIG. 20 shows a flowchart of a method for operating an implantable therapeutic substance delivery device 30 having a permanent magnet solenoid pump 48 embodiment. Generally, therapeutic substance delivery device 30 embodiments begin operation by having electronics 46 programmed to operate the permanent solenoid pump 48 to deliver therapeutic substance 36 at a programmed rate. The therapeutic substance 36 is supplied from a therapeutic substance reservoir 42 to a therapeutic substance inlet 76. The solenoid pump 48 generally operates by retracting a pump piston 58 and then actuating the pump piston 58 while operating valves to deliver therapeutic substance 36 through an infusion outlet 54 at a programmed rate. This operation is repeated a predetermined number of times at predetermined intervals to delivery therapeutic substance 36 at the programmed rate. For example, a solenoid pump 48 with a stroke volume of 2.0 micro liters would typically be operated from a maximum of about 10 cycles per second (Hz) to achieve an infusion rate of 1.2 milliliters per minute to a minimum of about 1.0 cycle per hour to achieve an infusion rate of about 48 micro liters per day.

Retracting the pump piston 58 is initiated when a first coil 68 for current flow in a first direction is energized 112 and a second coil 70 for current flow in an opposite direction are energized 112 to create a electromagnetic axial force. The pump piston 58 is retracted 114 when the electromagnetic axial forces acts on a permanent magnet 66 carried on the pump piston 58. While the pump piston 58 is retracting, an inlet valve 62 is opened 116 and a biasing element 60 is loaded. A pump chamber 88 is filled with therapeutic substance 36 through the inlet valve 62 while the pump piston 58 is being retracted 114. In an embodiment having a piston seal 78, during pump piston 58 retraction the piston seal 78 can also be configured to dampen the shock when the pump piston 58 reaches its fully retracted position. By dampening this shock, the piston seal 78 can reduce some wear and noise that occurs when the pump piston 58 reaches its fully retracted position. In embodiments having an anti-cavitation valve 90, the anti-cavitation valve 90 prevents therapeutic substance 36 in the inlet chamber 86 from flowing back to the therapeutic substance reservoir 42 when the pump piston 58 retracts. The anti-cavitation valve 90 helps maintain higher pump chamber 88 pressures during pump piston 58 retraction, which makes it easier to pass air bubbles.

During pump piston 58 retraction assuming there is anti-cavitation valve 90 and both the inlet chamber 86 and pump chamber 88 are filled with therapeutic substance 36, the pressure in the inlet chamber 86 will increase rapidly due to the incompressibility of liquids which will cause the therapeutic substance 36 to flow through the piston fluid path 84 into the pump chamber 88 without causing the pump chamber 88 pressure to decrease to the level that would cause gasses to come out of solution. After the pump piston 58 is retracted, operation of the solenoid pump 48 continues when the pump piston 58 is actuated.

Actuating the pump piston is initiated when the first coil 68 for current flow in the first direction is de-energized 122, and the second coil 70 for current flow in the opposite direction is de-energized 122 to collapse the electromagnetic axial force. As the electromagnetic axial force collapses, the biasing element 60 is unloaded, and the pump piston 58 is actuated by the biasing element 60 driving the pump piston 58 toward the outlet enclosure 74. While the pump piston 58 is being actuated 126, pressure generated in the pumping chamber 88 opens the outlet valve 64. The open outlet valve 64 permits a stroke volume to be expulsed through the infusion outlet 54 while the pump piston 58 is actuated 126. The therapeutic substance 36 discharged through the infusion outlet 54 is delivered at a programmed rate. In some embodiments during pump piston actuation 126, the piston seal 78 substantially prevents therapeutic substance 36 from flowing around the pump piston 58 back into the inlet chamber 86. The previously discussed method embodiment elements are presented in a general sequence that is intended to be limiting only when a particular element is required to be sequence in a certain way for the entire method embodiment to be practical. Pump piston actuation 126 can be mathematically characterized.

During piston actuation 126 to expulse therapeutic substance 36, when the pump chamber 88 volume is decreasing and the inlet chamber 86 volume is increasing the following relationships exist. The final pressure in the pump chamber 88 can be express as $P_{pc\,final}=$ $$\frac{P_{pc\,initial}}{CR_{pc}}$$

(Equation 3) where $P_{pc\,final}$ is the final pressure in the pump chamber 88, $P_{pc\,initial}$ is the initial pressure in the pump chamber 88, and $CR_{pc}$ is the compression ratio in the pump chamber 88. The final pressure in the inlet chamber 86 can be expressed as $$P_{ic\,final} = \frac{P_{ic\,initial}}{CR_{ic}}$$

(Equation 4) where $P_{ic\,final}$ is the final pressure in the inlet chamber 86, $P_{ic\,initial}$ is the initial pressure in the inlet chamber 86, and $CR_{ic}$ is the compression ratio in the pump chamber 88. Therapeutic substance 36 flows through the outlet valve 64 when $P_{pc\,final} \geq P_a + P_{ovc}$ (Equation 5) where $P_{ic}$ is the initial pressure in the inlet chamber 86, $P_a$ is the ambient pressure at the pump outlet, and $P_{ovc}$ is outlet valve 64 cracking (opening) pressure. The above relationships assume that there is an anti-cavitation valve 90, there is no air in the pump chamber 88, and since liquids are essential incompressible $P_{ic}$ decreases as the pump piston 58 is actuated.

Thus, embodiments of the solenoid pump 48 are disclosed to increase energy efficiency, increase accuracy, reduce the residential space requirement, improve therapeutic substance compatibility, and provide many other improvements. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An implantable therapeutic substance delivery device comprising:
   a first housing adapted for subcutaneous implantation, the first housing comprising an implantable, hermetically sealed unit;
   a second housing adapted for subcutaneous implantation, the second housing comprising an implantable, hermetically sealed unit;
   a coupling connecting the first housing to the second housing;
   a fluid reservoir located within one of the first housing and the second housing;
   control electronics located within one of the first housing and the second housing;
   a power source located within one of the first housing and the second housing, the power source operably connected to the control electronics;
   an infusion outlet located on one of the first housing and the second housing; and
   a solenoid pump mechanism located within one of the first housing and the second housing, wherein the pump mechanism comprises a piston and is operably connected to the fluid reservoir and the infusion outlet such that the pump mechanism is capable of delivering a therapeutic substance in the fluid reservoir to the infusion outlet;
   wherein the pump mechanism and the fluid reservoir are not in the same housing.

2. A device according to claim 1, wherein the fluid reservoir is located within the first housing, and wherein the control electronics, the power source, and the pump mechanism are all located within the second housing.

3. A device according to claim 2, wherein the coupling comprises a fluid coupling operably connecting the fluid reservoir and the pump mechanism.

4. A device according to claim 2, further comprising a refill port located in the first housing, wherein the refill port is operably coupled to the fluid reservoir.

5. A device according to claim 1, wherein the coupling comprises a fluid coupling.

6. A device according to claim 1, further comprising a refill port located in one of the first housing or the second housing, wherein the refill port is operably coupled to the fluid reservoir.

7. A device according to claim 1, wherein the control electronics, the power source, and the pump mechanism are all located within one of the first housing or the second housing.

8. A device according to claim 1, wherein the pump mechanism is located in the first housing and the fluid reservoir is located in the second housing.

9. A device according to claim 1, wherein the first housing and the second housing are adapted for subcutaneous implantation on the head of a subject.

10. An implantable therapeutic substance delivery device comprising:
    a first housing, the first housing comprising an implantable, hermetically sealed unit;
    a second housing, the second housing comprising an implantable, hermetically sealed unit;
    a fluid reservoir located within one of the first housing and the second housing;
    control electronics located within one of the first housing and the second housing;
    a power source located within one of the first housing and the second housing, the power source operably connected to the control electronics;
    a pump mechanism located within one of the first housing and the second housing, wherein the pump mechanism comprises a solenoid pump comprising a piston;
    a fluid coupling extending between the first housing to the second housing, wherein the fluid coupling operably connects the fluid reservoir and the pump mechanism; and
    an infusion outlet located on one of the first housing and the second housing, wherein the pump mechanism is operably connected to the fluid reservoir and the infusion outlet such that the pump mechanism is capable of delivering a therapeutic substance in the fluid reservoir to the infusion outlet.

11. A device according to claim 10, further comprising a refill port located in one of the first housing or the second housing, wherein the refill port is operably coupled to the fluid reservoir.

12. A device according to claim 10, wherein the first housing and the second housing are each adapted for subcutaneous implantation in the head.

13. A device according to claim 10, wherein the control electronics, the power source, and the pump mechanism are all located within one of the first housing or the second housing.

14. A device according to claim 10, wherein the fluid reservoir is located within the first housing, and wherein the control electronics, the power source, and the pump mechanism are all located within the second housing.

15. An implantable therapeutic substance delivery device comprising:
    a first housing adapted for subcutaneous implantation, the first housing comprising an implantable, hermetically sealed unit;
    a second housing adapted for subcutaneous implantation, the second housing comprising an implantable, hermetically sealed unit;
    a fluid reservoir located within the first housing;
    control electronics located within the second housing;

a power source located within the second housing, the power source operably connected to the control electronics;

a pump mechanism located within the second housing, wherein the pump mechanism comprises a solenoid pump comprising a piston;

an infusion outlet located on the second housing, wherein the pump mechanism is operably connected to the fluid reservoir and the infusion outlet such that the pump mechanism is capable of delivering a therapeutic substance in the fluid reservoir to the infusion outlet; and a fluid coupling extending between the first housing to the second housing, wherein the fluid coupling operably connects the fluid reservoir and the pump mechanism.

16. A device according to claim 15, wherein the first housing and the second housing are adapted for subcutaneous implantation on the head of a subject.

17. A method for infusing a therapeutic substance to an internal infusion site, the method comprising:

subcutaneously implanting a therapeutic substance delivery device, wherein the device comprises:

a first housing comprising an implantable, hermetically sealed unit subcutaneously implanted in a subject;

a second housing comprising an implantable, hermetically sealed unit subcutaneously implanted in the subject;

a fluid reservoir located within the first housing, the fluid reservoir comprising a therapeutic substance located therein;

control electronics located within the second housing;

a power source located within the second housing, the power source operably connected to the control electronics;

a solenoid pump mechanism comprising a piston, the solenoid pump mechanism located within the second housing; and subcutaneously implanting a coupling extending between the first housing and the second housing;

operating the pump mechanism to deliver the therapeutic substance in the fluid reservoir to an infusion site located outside of the first housing and the second housing, wherein the therapeutic substance passes from the fluid reservoir to the pump mechanism through the coupling; and controlling the pump mechanism using the control electronics.

18. A method according to claim 17, further comprising delivering the therapeutic substance to the fluid reservoir through a refill port located in one of the first housing or the second housing, wherein the refill port is operably coupled to the fluid reservoir.

19. A method according to claim 17, wherein the control electronics, the power source, and the pump mechanism are all located within the second housing.

20. A method according to claim 17, wherein the first housing and the second housing are subcutaneously implanted on the head of the subject.

* * * * *